US011173184B2

(12) United States Patent
Petri et al.

(10) Patent No.: US 11,173,184 B2
(45) Date of Patent: Nov. 16, 2021

(54) *BACILLUS SUBTILIS* STRAIN WITH PROBIOTIC ACTIVITY

(71) Applicant: Evonik Operations GmbH, Essen (DE)

(72) Inventors: Daniel Petri, Vienna (AT); Stefan Pelzer, Gütersloh (DE); Jessica Kleinbölting, Bielefeld (DE); Stella Molck, Bielefeld (DE); Maike Kipker, Essen (DE); Claudia Borgmeier, Bensheim (DE); Sandra Herbold, Mannheim (DE); Guido Meurer, Seeheim-Jugenheim (DE); Rose Whelan, Offenbach (DE); Kiran Doranalli, Frankfurt (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 15/607,534

(22) Filed: May 29, 2017

(65) Prior Publication Data

US 2017/0340683 A1 Nov. 30, 2017

(30) Foreign Application Priority Data

May 31, 2016 (EP) .................................... 16172164
Oct. 27, 2016 (EP) .................................... 16196025

(51) Int. Cl.

| | |
|---|---|
| ***A61K 35/742*** | (2015.01) |
| ***C12N 1/20*** | (2006.01) |
| ***A61K 35/00*** | (2006.01) |
| ***A01N 63/00*** | (2020.01) |
| *A01N 63/22* | (2020.01) |
| *C12R 1/125* | (2006.01) |

(52) U.S. Cl.

CPC .............. *A61K 35/742* (2013.01); *C12N 1/20* (2013.01); *C12N 1/205* (2021.05); *A01N 63/22* (2020.01); *A61K 35/00* (2013.01); *A61K 2035/115* (2013.01); *C12R 2001/125* (2021.05)

(58) Field of Classification Search

None

See application file for complete search history.

(56) References Cited

U.S. PATENT DOCUMENTS

| | | | | |
|---|---|---|---|---|
| 4,919,936 | A | 4/1990 | Iwanami et al. | |
| 5,227,294 | A * | 7/1993 | Carrera | C07K 7/06 435/252.31 |
| 6,060,051 | A | 5/2000 | Heins et al. | |
| 6,194,193 | B1 | 2/2001 | Drahos et al. | |
| 6,849,256 | B1 | 2/2005 | Farmer | |
| 7,247,299 | B2 | 7/2007 | Lin et al. | |
| 7,981,659 | B2 * | 7/2011 | Kadoya | C12N 9/2417 435/252.3 |
| 9,622,484 | B2 | 4/2017 | Taghavi et al. | |
| 9,844,573 | B2 | 12/2017 | Nielsen et al. | |
| 10,138,444 | B2 | 11/2018 | Ayangbile et al. | |
| 10,736,925 | B2 | 8/2020 | Huu et al. | |
| 2014/0010792 | A1 | 1/2014 | Rehberger et al. | |
| 2014/0065672 | A1 * | 3/2014 | Brune | C12P 21/02 435/69.1 |
| 2014/0342437 | A1 | 11/2014 | Carpenter et al. | |
| 2020/0113952 | A1 | 4/2020 | Pelzer et al. | |

FOREIGN PATENT DOCUMENTS

| | | | |
|---|---|---|---|
| EP | 0 287 699 | 10/1988 | |
| EP | 1 576 120 | 8/2009 | |
| JP | 2000-135096 | 5/2000 | |
| JP | 2003-190993 | 7/2003 | |
| JP | 2015-513910 | 5/2015 | |
| KR | 101467250 B1 * | 12/2014 | |
| WO | WO 98/28408 | 7/1998 | |
| WO | WO 00/43503 | 7/2000 | |
| WO | WO 03/066847 | 8/2003 | |
| WO | WO-2013151361 A1 * | 10/2013 | A23K 10/18 |
| WO | WO 2016/108974 | 7/2016 | |
| WO | WO 2017/048636 | 3/2017 | |
| WO | WO 2017/207371 | 12/2017 | |
| WO | WO 2017/207372 | 12/2017 | |
| WO | WO 2019/002471 | 1/2019 | |
| WO | WO 2019/002476 | 1/2019 | |
| WO | WO 2019/038153 | 2/2019 | |
| WO | WO 2019/063669 | 4/2019 | |

OTHER PUBLICATIONS

Ohno, Akihiro; et al; "Production of a Lipopeptide Antibiotic, Surfactin, by Recombinant Bacillus subtilis in Solid State Fermentation" Biotechnology and Bioengineering, 47, 209-214, 1995 (Year: 1995).*

Selvam, R; et al.; "Effect of Bacillus subtilis PB6, a natural probiotic on colon mucosal inflammation and plasma cytokines levels in inflammatory bowel disease" Indian Journal of Biochemistry & Biophysics, 46, 79-85, 2009 (Year: 2009).*

Jayaraman, Satishkumar; et al.; "Bacillus subtilis PB6 improves intestinal health of broiler chickens challenged with Clostridium perfringens-induced necrotic enteritis" Poultry Science, 92, 370-374, 2013 (Year: 2013).*

Hoang, Tran H; et al; "Recombinant Bacillus subtilis Expressing the Clostridium perfringens Alpha Toxoid Is a Candidate Orally Delivered Vaccine against Necrotic Enteritis" Infection and Immunity, 76, 5257-5265, 2008 (Year: 2008).*

Nithya, Vadakedath; Halami, Prakash M; "Evaluation of the probiotic characteristics of *Bacillus* species isolated from different food sources" Annals of Microbiology, 63, 129-137, 2013 (Year: 2013).*

Gao,. Xin; et al.; "Isolation of Bacillus subtilis: screening for aflatoxins B1, M1, and G1 detoxification" European Food Research Technology, 232, 957-962, 2011 (Year: 2011).*

(Continued)

*Primary Examiner* — David W Berke-Schlessel

(74) *Attorney, Agent, or Firm* — Law Office of Michael A. Sanzo, LLC

(57) ABSTRACT

The current invention concerns a new *B. subtilis* strain with strong inhibition of *C. perfringens* and its use as a probiotic.

21 Claims, No Drawings

Specification includes a Sequence Listing.

(56) References Cited

OTHER PUBLICATIONS

European Search Report for corresponding European application EP 16 17 2164 dated Nov. 28, 2016.
Allaart, et al., "Net B-producing and beta2-producing *Clostridium perfringens* associated with subclinical necrotic enteritis in laying hens in the Netherlands," *Avian Pathology* 41(6):541-546.
Argenzio, R.A., Secretion of the Stomach and Accessory Glands, p. 405-418. In: Reece, W.O. (ed.), Duke's Physiology of Domestic Animals; Twelfth Edition, Chapter 25; Cornell University Press, Ithaca, New York, (2004).
Argenzio, R.A., Digestive and Absorptive Functions of the Intestines, p. 419-437. In: Reece, W.O. (ed.), Duke's Physiology of Domestic Animals; Twelfth Edition, Chapter 26; Cornell University Press, Ithaca, New York, (2004).
Chen, et al., "Structural and Functional Characterization of Three Polyketide Synthase Gene Clusters in *Bacillus amyloliquefaciens* FZB 42," *Journal of Bacteriology* 188(11):4024-4036 (Jun. 2006).
Collins, et al., "*Streptococcus gallinaceus* sp. nov., from chickens," *International Journal of Systematic and Evolutionary Microbiology* 52:1161-1164 (2002).
Cutting, et al., Sporulation, germination and outgrowth. In: Harwood C R, Cutting S M editors. Molecular Biological Methods for *Bacillus*. Chichester, England: John Wiley & Sons, Ltd.; pp. 27-74 (1990).
Den Besten, et al., "Phenotypic and Transcriptomic Analyses of Mildly and Severly Salt-Stressed *Bacillus cereus* ATCC 14579 Cells," *Applied and Environmental Microbiology* 75(12):4111-4119 (Jun. 2009).
Glaser, et al., "Identification and Isolation of a Gene Required for Nitrate Assimilation and Anaerobic Growth of *Bacillus subtilis,"* *Journal of Bacteriology* 177(4):1112-1115 (Feb. 1995).
Goyette-Desjardins, et al., "*Streptococcus suis*, an important pig pathogen and emerging zoonotic agent—an update on the worldwide distribution based on serotyping and sequence typing," *Emerging Microbes and Infections* 3(6): e45 (published online Jun. 2014).
Hossain, et al., "Effect of *Bacillus subtilis, Closfridium butyricum* and *Lactobacillus acidophilus* endospores on growth performance, nutrient digestibility, meat quality, relative organ weight, microbial shedding and excreta noxious gas emission in broilers," *Veterinarni Medicinia* 60(2):77-86 (Feb. 2015).
Larsen, et al., "Characterization of *Bacillus* spp. strains for use as probiotic additives in pig feed," *Appl. Microbiol. Biotechnol.* 98:1105-1118 (Published online Nov. 2013).
Lumpkins, et al., "Evaluation of Distillers Dried Grains with Solubles as a Feed Ingredient for Broilers," *Poultry Science* 83:1891-1896 (accepted for publication Jul. 2004).
M'Sadeq, et al., "Towards the control of necrotic enteritis in broiler chickens with in-feed antibiotics phasing-out worldwide," *Animal Nutrition* 1:1-11 (Nov. 2015).
Palop, et al., "Influence of pH on heat resistance of *Bacillus licheniformis* in buffer and homogenised foods," *International Journal of Food Microbiology* 29:1-10 (Feb. 1996).
Parente, et al., "A comparison of methods for the measurement of bacteriocin activity," *Journal of Microbiological Methods* 22:95-108 (Apr. 1995).
Rushen, et al., "Animal Behavior and Well-Being Symposium: Farm animal welfare assurance: Science and application," *J. Anim. Sci*. 89:1219-1228 (2011).
Savva, et al., "Molecular Architecture and Functional Analysis of NetB, a Pore-forming Toxin from *Closfridium perfringens," JBC* 288(5):3512-3522 (Feb. 2013).
Scholz, et al., "Plantazolicin, a Novel Microcin B17/Streptolysin S-Like Natural Product from *Bacillus amyloliquefaciens* FZB42," *Journal of Bacteriology* 193(1):215-224 (Jan. 2011).
Songer, et al., "Clostridial enteric infections in pigs," *J. Vet. Diagn. Invest*. 17:528-536 (2005).
Teo, et al., "Inhibition of *Clostridium perfringens* by a Novel Strain of *Bacillus subtilis* Isolated from the Gastrointestinal Tracts of Healthy Chickens," *Applied and Environmental Microbiology* 71(8):4185-4190 (Aug. 2005).
Timbermont, et al., "Necrotic enteritis in broilers: an updated review on the pathogensis," *Avian Pathology* 40(4):341-347 (Aug. 2011).
Trampel, et al., Avian Digestion, pp. 488-500. In: Reece, W.O. (ed), Duke's Physiology of Domestic Animals; Twelfth Edition, Chapter 29; Cornell University Press, Ithaca, New York, USA (2004).
Uzal, et al., "Towards an understanding of the role of *Clostridium perfringens* toxins in human and animal disease," *Future Microbiol*. 9(3):361-377 (2014).
International Search Report for PCT/EP2017/062495 filed May 24, 2017, corresponding to copending U.S. Appl. No. 16/305,811.
Written Opinion of the International Searching Authority for PCT/EP2017/062495 filed May 24, 2017, corresponding to copending U.S. Appl. No. 16/305,811.
International Preliminary corresponding Report on Patentability for PCT/EP2017/062495 filed May 24, 2017, corresponding to copending U.S. Appl. No. 16/305,811.
Knap. et al., "*Bacillus licheniformis* Prevents Necrotic Enteritis in Broiler Chickens," *Avian Diseases* 54:931-935 (2010).
Reddy, et al., "Effective feather degradation and keratinase production by *Bacillus pumilus* GRK for its application as bio-detergent additive," *Bioresourse Technology* 243:254-263 (Jun. 2017).
Wang, et al., "Comparison of gyrB gene sequences, 16S rRNA gene sequences and DNA-DNA hybridization in the *Bacillus subtilis* group," *Journal of Systematic and Evolutionary Microbiology* 57(8):1846-1850 (Aug. 2007).
XP-002764349; Bacillus licheniforms strain BCRC 15413 a6S ribosomal RNA gene, partial sequence, last updated Aug. 14, 2007.
Zhou, et al., "Effects of *Bacillus licheniforms* on the growth performance and expression of lipid metabolism-related genes in broiler chickens challenged with *Clostridium perfringens*-induced necrotic enteritis," *Lipids in Health and Disease* 15:48; pp. 1-10 (Jan. 2016).
U.S. Appl. No. 16/305,811, filed Nov. 29, 2018, Petri.
Bacillus subtilis 16S rDNA sequence; NCBI Reference Sequence: NR_112116.2; retrieved Feb. 8, 2020.
Bacillus subtilis groEL sequence; NCBI Reference Sequence: NR_000964.3; retrieved Feb. 8, 2020.
Bacillus subtilis gyrB sequence; NCBI Reference Sequence: NR_000964.3; retrieved Feb. 8, 2020.
Bacillus subtilis rpoB sequence; NCBI Reference Sequence: NR_000964.3; retrieved Feb. 8, 2020.
Bacillus subtilis ygfD sequence; GenBank: D84432.1; retrieved Feb. 8, 2020.
U.S. Appl. No. 16/627,195, filed Dec. 27, 2019, Pelzer.
International Search Report for PCT/EP2018/067422, filed Jun. 28, 2018; corresponding to copending U.S. Appl. No. 16/627,195.
Written Opinion of the International Searching Authority for PCT/EP2018/067422, filed Jun. 28, 2018; corresponding to copending U.S. Appl. No. 16/627,195.
International Preliminary Report on Patentability PCT/EP2018/067422, filed Jun. 28, 2018; corresponding to copending U.S. Appl. No. 16/627,195.
Aluwong, et al., "Effect of Yeast Probiotic on Growth, Antioxidant Enzyme Activities and Malondialdehyde Concentration of Broiler Chickens," *Antioxidants* 2:326-339 (2013).
Beauchamp, et al., "Superoxide Dismutase: Improved Assays and an Assay Applicable to Acrylamide Gels," *Anal. Biochem*. 44:276-287 (1971).
Bradford, "A Rapid and Sensitive Method for the Quatitation of Microgram Quantities of Protein Utilizing the Principle of Protein-Dye Binding," *Anal. Biochem*. 72:248-254 (1976).
Kense, et al., "*Enterococcus cecorum* infections in broiler breeders and their offspring: molecular epidemiology," *Avian Pathology* 40(6):603-612 (2011).
Lin, et al., "Acute heat stress induces oxidative stress in broiler chickens," *Comparative Biochemistry and Physiology, Part A* 144:11-17 (2006).

(56) References Cited

OTHER PUBLICATIONS

Mishra, et al., "Probiotics as Potential Antioxidants: A Systematic Review," *J. Agric. Food Chem.* 63:3615-3626 (2015).
Oelschlaeger, "Mechanisms of probiotic action—A review," *International Journal of Medical Microbiology* 300:57-62 (2010).
Songer, et al., "Infection of neonatal swine with *Clostridium difficile,*" *Swine Health Prod.* 8(4):185-189 (2000).
Woodbury, et al., "An Improved Procedure Using Ferricyanide for Detecting Catalase Isozymes," *Anal. Biochem.* 44:301-305 (1971).
International Search Report for WO 2017/207372 (PCT/EP2017/062497), filed May 24, 2017.
Written Opinion of the International Searching Authority for WO 2017/207372 (PCT/EP2017/062497), filed May 24, 2017.
International Preliminary Report on Patentability for WO 2017/207372 (PCT/EP2017/062497), filed May 24, 2017.
Bampidis, et al., (EFSA Panel on Additives and Products or Substrates used in Animal Feed), "Safety and efficacy of *Bacillus subtilis* PB6 (*Bacilus velezensis* ATCC PTA-6737) as a feed additive for chickens for fattening, chickens reared for laying, minor poultry species (except for laying purposes), ornamental, sporting and game birds," *ESFA Journal* 18(11):6280 pp. 1-10 (adopted Sep. 2020).
Hong, et al., "The use of bacterial spore formers as probiotics," *FEMS Microbiology Reviews* 29:813-835 (published online Dec. 2004).
"Bacillus subtilis strain UD1022, complete genome," Feb. 28, 2016; retrieved from the internet Mar. 31, 2021; https://www.ncbi.nlm.nih.gov/nuccore/CP011534.1?report=fasta.
Japanese Office Action for corresponding Japanes patent application 2018-562615, dated Feb. 1, 2021.
Bishnoi, et al., "Draft Genome Sequence of a Natural Root Isolate, *Bacillus subtilis* UD1022, a Potential Plant Growth-Promoting Biocontrol Agent," *Genome Announcements* 3(4):e00696-15 (Jul./Aug. 2015).

* cited by examiner

SEQUENCE LISTING

```
<160> NUMBER OF SEQ ID NOS: 5

<210> SEQ ID NO 1
<211> LENGTH: 1538
<212> TYPE: DNA
<213> ORGANISM: Bacillus subtilis

<400> SEQUENCE: 1
```

-continued

```
agagtttgat cctggctcag gacgaacgct ggcggcgtgc ctaatacatg caagtcgagc     60
ggacagatgg gagcttgctc cctgatgtta gcggcggacg ggtgagtaac acgtgggtaa    120
cctgcctgta agactgggat aactccggga aaccggggct aataccggat ggttgtttga    180
accgcatggt tcaaacataa aaggtggctt cggctaccac ttacagatgg acccgcggcg    240
cattagctag ttggtgaggt aacggctcac caaggcaacg atgcgtagcc gacctgagag    300
ggtgatcggc cacactggga ctgagacacg gcccagactc ctacgggagg cagcagtagg    360
gaatcttccg caatggacga aagtctgacg gagcaacgcc gcgtgagtga tgaaggtttt    420
cggatcgtaa agctctgttg ttagggaaga acaagtaccg ttcgaatagg gcggtacctt    480
gacggtacct aaccagaaag ccacggctaa ctacgtgcca gcagccgcgg taatacgtag    540
gtggcaagcg ttgtccggaa ttattgggcg taaagggctc gcaggcggtt tcttaagtct    600
gatgtgaaag cccccggctc aaccggggag ggtcattgga aactggggaa cttgagtgca    660
gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttaggggg    840
tttccgcccc ttagtgctgc agctaacgca ttaagcactc cgcctgggga gtacggtcgc    900
aagactgaaa ctcaaaggaa ttgacggggg cccgcacaag cggtggagca tgtggtttaa    960
ttcgaagcaa cgcgaagaac cttaccaggt cttgacatcc tctgacaatc ctagagatag   1020
gacgtcccct tcgggggcag agtgacaggt ggtgcatggt tgtcgtcagc tcgtgtcgtg   1080
agatgttggg ttaagtcccg caacgagcgc aacccttgat cttagttgcc agcattcagt   1140
tgggcactct aaggtgactg ccggtgacaa accggaggaa ggtggggatg acgtcaaatc   1200
atcatgcccc ttatgacctg ggctacacac gtgctacaat ggacagaaca aagggcagcg   1260
aaaccgcgag gttaagccaa tcccacaaat ctgttctcag ttcggatcgc agtctgcaac   1320
tcgactgcgt gaagctggaa tcgctagtaa tcgcggatca gcatgccgcg gtgaatacgt   1380
tcccgggcct tgtacacacc gcccgtcaca ccacgagagt ttgtaacacc cgaagtcggt   1440
gaggtaacct tttaggagcc agccgccgaa ggtgggacag atgattgggg tgaagtcgta   1500
acaaggtagc cgtatcggaa ggtgcggctg gatcacct                           1538
```

```
<210> SEQ ID NO 2
<211> LENGTH: 1197
<212> TYPE: DNA
<213> ORGANISM: Bacillus subtilis

<400> SEQUENCE: 2
```

```
gtgaaaaata aatggctgtc tttttttcg ggtaaggtcc agcttgaatt gacgggaaga     60
gggattgagc ggctccttaa tgaatgcaca agacagggga ttccggtctt tcatgtcaaa    120
aaaaagaaag aagccgtatc gttatatata cagcttcagg atgtacatgc ctttcggcgg    180
gtaagaagta aatttaaatg taaagcccga tttatcaatc ggaagggatt tcccttcctg    240
ttgctgaaat caaagctgaa tatagggttt acgatcggtt ttgcgatttt tttcattctt    300
ttgtttttgc tgtccaatat ggtgtggaaa attgatgtga caggcgctaa gcctgaaaca    360
gaacatcaaa tgaggcagca tcttaatgaa atcggcgtca aaaagggccg tctgcagttt    420
ttaatgatgt cgcccgaaaa aatacagaaa tcattaacca atggaataga caatatcact    480
tgggtcggag ttgatctgaa ggggacgacc attcatatga aagttgtgga gaaaaatgag    540
```

```
cccgaaaaag aaaaatatgt tagcccgcgc aatattgtcg ccaaaaagaa agcaaccatt    600

acgagaatgt ttgtgcaaaa aggacagccc atggccgcca tacacgatca tgttgaaaag    660

ggacagctgc ttgtttcggg actgatcggc agcgaagacc atcagcagga agtcgcctca    720

aaagcagaaa tttatggaga aacctggtat agatcagaag tgacagtccc gcttgaaaca    780

ttatttaacg tctatacggg caaagtaagg acaaagcaca agctttcttt tggttctttg    840

gcaatcccga tctgggggat gacgtttaaa aaagaggaat tgaagcatcc aaaaacagaa    900

caagaaaagc attcgcttca ttttctcgga tttaagctcc ctgtatccta tgtcaaagag    960

caaacgagag aaagtgaaga ggctttgcga aaatatacaa aagaagaagc agttcaagaa   1020

ggcattaaat tgggtaaaca ggatgtagag gataaaatag gcgaaaacgg cgaggtgaaa   1080

agtgaaaaag ttttgcacca gactgttgag aatggtaaag taaagttgat tattctctac   1140

caagttatag aagatatcgt tcaaaccaca cctattgtca gggagactga agaatga      1197
```

<210> SEQ ID NO 3
<211> LENGTH: 1923
<212> TYPE: DNA
<213> ORGANISM: Bacillus subtilis

<400> SEQUENCE: 3

```
gtggctatgg aacagcagca aaacagttat gatgaaaatc agatacaggt actagaagga     60

ttggaagctg ttcgtaaaag accggggatg tatatcggtt cgacaaacag caaaggcctt    120

caccacctgg tatgggaaat tgtcgacaat agtattgacg aagccctcgc cggttattgt    180

acggatatca atatccaaat cgaaaaagac aacagtatca cggttgtaga taatggccgc    240

ggtattccag tcggtattca tgaaaaaatg ggccgtcctg cggtagaagt cattatgacg    300

gtacttcatg ccggaggaaa atttgacgga agcggctata aagtatccgg aggattacac    360

ggtgtaggtg cgtctgtcgt aaacgcacta tcaacagagc ttgatgtgac ggttcaccgt    420

gacggtaaaa ttcaccgcca aacttataaa cgcggagttc cggttacaga ccttgaaatc    480

attggcgaaa cggatcatac aggaacgacg acacattttg tcccggaccc tgaaattttc    540

tcagaaacaa ccgagtatga ttatgatctg cttgccaacc gcgtacgtga attagccttt    600

ttaacaaagg gcgtaaacat cacgattgag gataaacgtg aaggacaaga gcgcaaaaat    660

gaataccatt acgaaggcgg aattaaaagt tatgtagagt atttaaaccg ctctaaagag    720

gttgtccatg aagagccgat ttacattgaa ggcgaaaagg acggcattac ggttgaagtg    780

gctttgcaat acaatgacag ctacacaagc aacatttact cgtttacaaa caacattaac    840

acgtacgaag gcggtaccca tgaagctggc ttcaaaacgg gcctgactcg tgttatcaac    900

gattacgcca gaaaaaaagg gcttattaaa gaaaatgatc caaacctaag cggagatgac    960

gtaagggaag ggctgacagc gattatttca atcaaacacc ctgatccgca gtttgagggc   1020

caaacgaaaa caaagctggg caactcagaa gcacggacga tcaccgatac gttattttct   1080

acggcgatgg aaacatttat gctggaaaat ccagatgcag ccaaaaaaat tgtcgataaa   1140

ggcttaatgg cggcaagagc aagaatggct gcgaaaaaag cccgtgaact aacacgtcgt   1200

aagagtgctt tggaaatttc aaacctgccc ggtaagttag cggactgctc ttcaaaagat   1260

ccgagcatct ccgagttata tatcgtagag ggtgactctg ccggaggatc tgctaaacaa   1320

ggacgcgaca gacatttcca agccattttg ccgcttagag gtaaaatcct aaacgttgaa   1380

aaggccagac tggataaaat cctttctaac aacgaagttc gctctatgat cacagcgctc   1440

ggcacaggta ttggggaaga cttcaacctt gagaaagccc gttaccacaa agttgtcatt   1500
```

atgacagatg ccgatgttga cggcgcgcac atcagaacac tgctgttaac gttcttttac 1560
agatatatgc gccaaattat cgagaatggc tacgtgtaca ttgcgcagcc gccgctctac 1620
aaggttcaac aggggaaacg cgttgaatat gcgtacaatg acaaggagct tgaagagctg 1680
ttaaaaactc ttcctcaaac ccctaagcct ggactgcagc gttacaaagg tcttggtgaa 1740
atgaatgcca cccagctatg ggagacaacc atggatccta gctccagaac acttcttcag 1800
gtaactcttg aagatgcaat ggatgcggac gagacttttg aaatgcttat gggcgacaag 1860
gtagaaccgc gccgaaactt catagaagcg aatgcgagat acgttaaaaa tcttgacatc 1920
taa 1923

<210> SEQ ID NO 4
<211> LENGTH: 3582
<212> TYPE: DNA
<213> ORGANISM: Bacillus subtilis

<400> SEQUENCE: 4
ttgacaggtc aactagttca gtatggacga caccgccagc gcagaagcta tgctcgcatt 60
agcgaagtgt tagaattacc aaatctcatt gaaattcaaa cctcttctta tcagtggttt 120
cttgatgagg gtcttagaga gatgtttcaa gacatatcac caattgagga tttcactggt 180
aacctctctc ttgagttcat tgattatagt ttaggtgagc ctaaatatcc tgtagaggaa 240
tcaaaagaac gtgatgtgac ttactcagct ccgctaagag tgaaggttcg tttaattaac 300
aaagaaactg gagaggtaaa agaccaagat gtcttcatgg gtgatttccc tattatgaca 360
gatacaggta cttttatcat taacggtgcg gaacgtgtta ttgtttccca gcttgttcgg 420
tctccaagtg tatatttcag tggtaaagta gacaaaaacg gtaaaaaagg ttttaccgca 480
actgtcattc caaaccgtgg cgcatggtta gaatacgaaa ctgatgcgaa agatgttgtt 540
tatgtccgca ttgatcgcac acgtaagttg ccggttacgg ttcttttgcg tgctctcggc 600
ttcggctccg atcaagagat tcttgatctc ataggagaaa acgaatacct gcgaaatacg 660
cttgataaag ataacacaga aaacagtgac aaagcgttgc tggaaattta cgagcgtctc 720
cgtcctggag agccgcctac agtagaaaat gcgaaaagct tgcttgattc tcgtttcttt 780
gatccgaaac gatacgatct tgccaatgta ggacgctata aaattaataa aaaacttcat 840
attaagaatc gcctcttcaa tcagagactt gctgaaacgc ttgttgatcc tgaaacagga 900
gaaatccttg ctgaaaaagg ccagattctt gatagaagaa cacttgataa agtactgcca 960
tacttagaaa acggaatcgg ttttagaaag ctgtatccga atggcggcgt tgttgaagat 1020
gaagtgactc ttcaatcaat taaaatcttt gctccgactg atcaagaagg agaacaggtt 1080
attaatgtaa tcggcaatgc ttacatcgaa gaagagatta aaaacatcac gcctgctgat 1140
attatttctt caatcagcta cttcttcaac ttgctgcacg gagtaggcga tacagatgat 1200
atcgatcatc ttggaaaccg ccgtttacgc tctgtaggcg agcttctcca gaaccaattc 1260
cgtatcggtt taagccgtat ggaacgtgtg gttcgtgaga gaatgtcaat tcaagatacg 1320
aatacaatta cgcctcagca gctgatcaat attcgtcctg ttattgcgtc cattaaagag 1380
ttctttggaa gctcacagct ttctcaattc atggatcaga cgaacccgct tgctgaatta 1440
acgcacaagc gtcgtctgtc agcattagga ccgggcggat tgacacgtga gcgtgccgga 1500
atggaagtgc gtgacgttca ctactcccac tatggccgta tgtgtccgat tgaaacgcct 1560
gagggcccga acatcggttt gatcaactca ctatcatctt atgcaaaagt aaaccgtttt 1620

-continued

```
ggctttattg aaacgccata tcgccgcgtt gaccctgaaa cagggaaggt aacgggcaga   1680
atcgattact taactgctga tgaagaggat aactatgttg tcgctcaagc gaatgctcgt   1740
cttgatgacg aaggcgcctt tattgatgac agcatcgtag ctcgtttccg cggggagaac   1800
actgttgttt ccagaaaccg tgtagactac atggatgtat cgcctaagca ggttgtatct   1860
gctgcgacag catgtatccc gttcttagaa aacgatgact cgaaccgtgc cctcatggga   1920
gcgaacatgc agcgccaggc tgtgcctttg atgcagccgg aagctccatt tgttggaact   1980
ggtatggaat acgtatcagg aaaagactct ggtgccgctg ttatttgtaa acaccctggt   2040
atcgttgaac gcgtagaagc gaaaaacgtt tgggttcgcc gttatgaaga agtagacggt   2100
caaaaagtaa aaggaaacct ggataaatac agcctgctga aatttgtccg ctctaaccaa   2160
ggtacgtgct acaaccagcg tccgatcgta agtgtcggcg atgaagtggt aaaaggagaa   2220
atccttgctg acggtccttc tatggagctt ggtgaacttg cacttggccg taacgtaatg   2280
gtcggcttca tgacatggga tggctacaac tatgaggatg ccatcatcat gagtgaacgc   2340
ctagtgaagg atgatgttta tacatctatc cacattgaag aatacgaatc agaagcacgt   2400
gatacgaaac ttggacctga agaaatcact cgcgatattc caaacgtcgg tgaagatgcg   2460
cttcgcaatc ttgatgaccg tggaatcatc cgtattgggg cagaagtaaa agacggagat   2520
cttcttgttg gtaaagtaac gcctaaaggc gtaactgaac tgactgcaga agaacgcctt   2580
cttcacgcca tttttggcga gaaagcccgc gaggttcgtg atacttctct tcgtgtgcct   2640
cacggcggcg gcggaattat ccatgacgtt aaagtcttca accgtgaaga cggagacgaa   2700
cttcctccag gtgttaacca gttagtacgc gtatatatcg ttcagaaacg taagatttct   2760
gaaggggata aaatggccgg tcgtcacggt aacaaaggtg ttatctctaa gattcttcct   2820
gaagaggata tgccttacct tcctgacggc acaccaattg atatcatgct taacccgctg   2880
ggcgtaccat cacgtatgaa catcgggcag gtattggaac ttcacatggg tatggccgct   2940
cgttaccttg gcattcacat tgcatctcct gtatttgacg gagcgcgaga agaggatgtc   3000
tgggaaacac ttgaagaagc cggcatgtct cgtgacgcca aaacagtgct ttacgacgga   3060
cgtactggag agccgtttga taaccgtgta tctgtcggta tcatgtacat gatcaaacta   3120
gctcacatgg ttgacgataa acttcatgca cgctctacag gtccttactc acttgttacg   3180
cagcagcctc ttggcggtaa agcgcaattt ggcggacagc gttttggtga gatggaggtt   3240
tgggcacttg aagcttacgg tgcggcttat actcttcaag aaattctgac tgttaagtct   3300
gatgacgtgg ttggacgtgt gaaaacatac gaagccatcg ttaaaggcga caatgttcct   3360
gaaccaggtg ttccggaatc attcaaagta ttaatcaaag aacttcaaag cttaggtatg   3420
gatgtcaaaa tcctttctgg tgatgaagaa gaaatagaaa tgagagattt agaagacgaa   3480
gaagatgcga aacaagctga cggcctggca ttatcaggtg atgaagagcc ggaagaaaca   3540
gcatctgcag acgttgaacg cgatgtagta acaaaagaat aa                      3582
```

<210> SEQ ID NO 5
<211> LENGTH: 1632
<212> TYPE: DNA
<213> ORGANISM: Bacillus subtilis

<400> SEQUENCE: 5

```
atggcaaaag aaattaagtt tagtgaagaa gctcgccgcg caatgcttcg cggtgtcgat     60
gcacttgctg atgctgttaa agtaacttta ggaccaaaag gacgcaacgt ggttctagag    120
aaaaaattcg gttctccgtt aatcacaaat gacggtgtaa caatcgctaa agaaatcgag    180
```

-continued

```
ctagaagacg cttttgaaaa catgggtgct aagcttgttg ctgaagtagc cagcaaaaca    240

aacgacgttg ccggtgacgg tacaacaact gcaacagttc ttgcgcaagc aatgatccgt    300

gaaggcctta aaaacgtaac agcaggcgct aaccctgtag gcgtgcgtaa agggatggaa    360

caagctgtag cggttgcgat cgaaaactta aaagaaattt ctaagccaat cgaaggcaaa    420

gagtctatcg ctcaggttgc tgcgatctct gctgctgacg aggaagtcgg aagccttatc    480

gctgaagcaa tggagcgcgt aggaaacgac ggcgttatca caatcgaaga gtctaaaggc    540

ttcacaactg agcttgaagt tgttgaaggt atgcaattcg accgcggata tgcgtctcct    600

tacatggtaa ctgactctga taagatggaa gcggttcttg acaatcctta catcttaatc    660

acagacaaaa aaatcacaaa cattcaagaa atccttcctg tgcttgagca ggttgttcag    720

caaggcaaac cattgcttct gatcgctgag gatgttgaag gcgaagcact tgcaacactt    780

gttgtgaaca aacttcgcgg cacattcaac gcagttgctg ttaaagctcc tggcttcggt    840

gaccgccgta aagcaatgct tgaagacatc gctgtcctta ctggcggaga agtcatcaca    900

gaagatcttg gccttgacct gaaatctact caaatcgctc aattgggacg cgcttctaaa    960

gttgtcgtta ctaaagaaaa cacaacaatc gttgaaggcg ctggcgaaac agacaaaatt   1020

tctgcccgcg tgactcaaat ccgcgctcaa gtggaagaaa caacttctga gttcgacaga   1080

gaaaaattac aagagcgtct tgcgaaactt gctggcggcg tagctgtcat caaagtcggc   1140

gctgcgactg aaactgagct gaaagagcgt aaacttcgca tcgaagacgc cttgaactca   1200

actcgcgcag ctgttgaaga aggcatcgta tccggtggtg gtacagcgct tgtaaacgta   1260

tataacaaag tcgctgcagt tgaagctgaa ggcgatgctc aaacaggtat caacatcgtg   1320

cttcgcgcgc ttgaagagcc aatccgtcaa atcgcacaca acgctggcct tgaaggatct   1380

gtcatcgttg agcgcctcaa aaacgaagaa atcggcgtag gcttcaacgc tgcaactggc   1440

gaatgggtaa acatgatcga aaaaggtatc gttgacccaa cgaaagttac acgctcagct   1500

cttcaaaacg ctgcgtctgt agctgcaatg ttcttaacta ctgaagctgt tgtcgctgac   1560

aagccagaag aaaacgctgg cggcggaatg cctgacatgg gcggcatggg cggtatgggc   1620

ggcatgatgt aa                                                       1632
```

*BACILLUS SUBTILIS* STRAIN WITH PROBIOTIC ACTIVITY

CROSS REFERENCE TO RELATED APPLICATIONS

The present application claims priority under 35 U.S.C. § 119 to European application EP16172164.2 filed on May 31, 2016 and to European application EP 16196025.7 filed on Oct. 27, 2016. The contents of each of these European applications is incorporated by reference in its entirety.

FIELD OF THE INVENTION

The current invention concerns a new *B. subtilis* strain with strong inhibition of *C. perfringens* and its use as probiotic.

BACKGROUND OF THE INVENTION

The use of *B. subtilis* strains as probiotic ingredient in the feed industry is well known in the art. The function of probiotics (also called "direct-fed microbials" or "DFM") is to influence the gut microflora in a positive way by supporting the growth of beneficial bacteria and/or the suppression of the growth of pathogenic bacteria. Ideally, by using probiotics the use of antibiotic growth promotors (AGPs) becomes redundant. It is also desirable for probiotics to fulfill other functions, e.g., helping in the digestion of specific feed ingredients. Thus, there is a need for probiotics which influence the gut microflora in a positive way and fulfill other functions.

DETAILED DESCRIPTION OF THE INVENTION

The present invention is directed to bacteria that are effective at inhibiting the growth of *C. perfringens*, the main commercially relevant pathogen of poultry, that show a very high proliferation rate in presence of bile and that help to digest cellulose in a very effective way.

*Bacillus subtilis* DSM 32315 was identified by screening naturally occurring isolates and was deposited on May 12, 2016 under the terms of the Budapest Treaty on the International Recognition of the Deposit of Microorganisms for the Purpose of Patent Procedure. Deposit was made by Evonik Degussa GmbH at the international depositary Leibniz Institute DSMZ-German Collection of Microorganisms and Cell Culture, Inhoffenstr. 7 B, D-38124 Braunschweig GERMANY, which assigned it Accession Number DSM 32315.

In a first embodiment, the current invention is directed to a *Bacillus subtilis* strain and preparations that contain or are derived from this strain. Specifically, the invention is directed to one or more of the following groups:

a) the *Bacillus subtilis* strain deposited under DSM 32315 at the DSMZ;
b) a mutant of the *Bacillus subtilis* strain deposited under DSM 32315 having all identifying characteristics of the strain DSM 32315, wherein the mutant preferably has a DNA sequence identity to DSM 32315 of at least 95%, preferably at least 96, 97 or 98%, and more preferably at least 99 or 99.5%;
c) a preparation containing (a) or (b);
d) a preparation containing an effective mixture of metabolites from (a), (b) or (c).

The *Bacillus subtilis* strain as deposited under DSM 32315 exhibits the following characterizing sequences:

a) a 16S rDNA sequence with a sequence identity of at least 99.5%, and preferably, 100%, to the polynucleotide sequence according to SEQ ID NO:1;
b) a yqfD sequence with a sequence identity of at least 99.5%, and preferably, 100%, to the polynucleotide sequence according to SEQ ID NO:2;
c) a gyrB sequence with a sequence identity of at least 99.5%, and preferably, 100%, to the polynucleotide sequence according to SEQ ID NO:3;
d) an rpoB sequence with a sequence identity of at least 99.5%, and preferably, 100%, to the polynucleotide sequence according to SEQ ID NO:4;
e) a groEL sequence with a sequence identity of at least 99.5%, and preferably, 100%, to the polynucleotide sequence according to SEQ ID NO:5.

Thus, a further subject of the current invention is a *Bacillus subtilis* strain or a preparation thereof, exhibiting at least one, and preferably all, of the following characteristics:

a) a 16S rDNA sequence with a sequence identity of at least 99%, preferably at least 99.5%, more preferably at least 99.8 or 99.9%, above all 100%, to the polynucleotide sequence according to SEQ ID NO:1;
b) a yqfD sequence with a sequence identity of at least 99%, preferably at least 99.5%, more preferably at least 99.8 or 99.9%, and most preferably 100%, to the polynucleotide sequence according to SEQ ID NO:2;
c) a gyrB sequence with a sequence identity of at least 99%, preferably at least 99.5%, more preferably at least 99.8 or 99.9%, and most preferably 100%, to the polynucleotide sequence according to SEQ ID NO:3.

Preferably, this *B. subtilis* strain exhibits at least one, and more preferably all, of the following further characteristics:

d) an rpoB sequence with a sequence identity of at least 99%, preferably at least 99.5%, more preferably at least 99.8 or 99.9%, and most preferably 100%, to the polynucleotide sequence according to SEQ ID NO:4;
e) a groEL sequence with a sequence identity of at least 99%, preferably at least 99.5%, more preferably at least 99.8 or 99.9%, and most preferably 100%, to the polynucleotide sequence according to SEQ ID NO:5.

Thus, a particular subject of the current invention is also a *Bacillus subtilis* strain, exhibiting the following characteristics:

a) a 16S rDNA sequence according to SEQ ID NO:1;
b) a yqfD sequence according to SEQ ID NO:2;
c) a gyrB sequence according to SEQ ID NO:3.

Preferably, this *B. subtilis* strain exhibits the following further characteristics:

d) an rpoB sequence according to SEQ ID NO:4;
e) a groEL sequence according to SEQ ID NO:5.

The strains of the current invention are preferably characterized by at least one, and more preferably by all, of the following further features:

They are preferably able to grow under anaerobic conditions. Further, they are preferably able to degrade water-insoluble cellulose as well as protein under such anaerobic conditions.

They preferably inhibit infectious bacteria, in particular *C. perfringens*, very effectively. In particular, they are preferably characterized by a pathogen clearance of at least 10 mm, more preferably at least 13 mm, in a well diffusion antagonism assay on LBKelly agar plates with respect to *C. perfringens* type strain ATCC 13124.

The spores are preferably viable at low pHs and preferably survive exposure to pHs as low as 4.0, in particular as low as 3.0, preferably as low as 2.0, for at least one hour.

The strains according to the invention are preferably further characterized by being able to grow in the presence of 0.05 wt.-% acetic acid, 0.05 wt.-% propionic acid and/or 0.2 wt.-% lactic acid.

They are preferably further characterized by a cellulase activity of at least 200 mU/mL, more preferably at least 300 mU/mL, still more preferably at least 350 mU/mL, and most preferably about 369 mU/mL, and by a xylanase activity of at least 15 mU/mL, more preferably at least 20 mU/mL, still more preferably at least 25 mU/mL, and most preferably about 33 mU/mL.

The *B. subtilis* strains according to the invention are further characterized by being able to grow in presence of 2 mM bile, more preferably in presence of 4 mM bile. They are also preferably characterized by an AUC5 performance value of at least 0.5, preferably at least 0.65, more preferably at least 0.8, and most preferably about 0.88, and an AUC10 performance value of at least 1.2, preferably at least 1.4, still more preferably, at least 1.6, and most preferably about 1.7, in the presence of 2 mM bile.

In addition, the strains are preferably able to grow under high salt conditions and, in particular in presence of 5 wt.-% of NaCl, for at least one day.

In addition, the strains of the current invention preferably survive the high temperatures necessary for pelleting animal feed, in particular, they preferably survive a temperature of 80° C. for at least 20 minutes.

Without wishing to be bound by any theory, it is thought that the *Bacillus subtilis* strains according to the current invention enhance animal health by a multifaceted mode of action, including the production of antibacterial metabolites with selective efficacy and the competition with pathogenic bacteria by better consuming the available nutrients, thereby suppressing effective establishment of pathogenic bacteria in the gut.

It is an advantage of probiotics in comparison to antibiotics, that they do not destroy bacteria indiscriminately and do not they lead to antibiotic resistant strains of pathogenic bacteria. Normally, they are able to selectively compete with pathogenic bacteria by production of antimicrobial substances with specific efficacy, and are ideally able to simultaneously enhance the growth and viability of beneficial gut microflora. Further, they are preferably able to stimulate a systemic immune response in the treated animals.

The mutant strains of DSM 32315 of the current invention are preferably spontaneous mutants. The term “spontaneous mutant” refers to mutants that arise from DSM 32315 without the intentional use of mutagens. Such spontaneous mutants may be obtained by classical methods, such as growing the *Bacillus subtilis* strain in the presence of UV light or in the presence of a certain antibiotic to which the parent is susceptible and testing any resistant mutants for improved biological activity or improved ability to enhance one or more of the indicia of animal health. Other methods for identifying spontaneous mutants are known to those of ordinary skill in the art. But besides these preferred spontaneous mutants all other kinds of mutants of DSM 32315, e.g., mutants obtained by genetic engineering, are also part of the current invention.

One particular embodiment of the current invention are mutants of the strain DSM 32315 that are not found in nature and that have mentioned above.

In a preferred embodiment of the current invention, the strains and preparations of the present invention are administered orally to animals or human beings.

Thus, a further subject of the current invention are compositions, such as feedstuffs, foodstuffs, drinking and rearing water as well as therapeutic compositions, containing a *B. subtilis* strain and/or a preparation of the current invention.

A further subject of the current invention is also the use of a *B. subtilis* strain and/or a preparation of the current invention as a probiotic ingredient (DFM) in feed or food products.

Preferred foodstuffs according to the invention are dairy products, in particular yoghurt, cheese, milk, butter and quark.

The cells of the strains of the current invention may be present, in particular in compositions as spores (which are dormant), as vegetative cells (which are growing), as transition state cells (which are transitioning from growth phase to sporulation phase) or as a combination of at least two, and preferably all of these types of cells. In a preferred embodiment, the composition of the current invention comprises mainly or only spores.

The *Bacillus subtilis* strains of the current invention and compositions containing them, when administered to animals, preferably enhance the health of such animals and/or improve the general physical condition of such animals and/or improve the feed conversion rate of such animals and/or decrease the mortality rate of such animals and/or increase the survival rates of such animals and/or improve the weight gain of such animals and/or increase the productivity of such animals and/or increase the disease resistance of such animals and/or increase the immune response of such animals and/or establish or maintain a healthy gut microflora in such animals and/or reduce the pathogen shedding through the feces of such animals. In particular the strains and compositions of the current invention might be used to assist in re-establishing a healthy balance of the gut microflora after administration of antibiotics for therapeutic purposes.

A further subject of the current invention is therefore a method of enhancing the health of animals and/or of improving the general physical condition of animals and/or of improving the feed conversion rate of animals and/or of decreasing the mortality rate of animals and/or of increasing the survival rates of animals and/or of improving the weight gain of animals and/or of increasing the productivity of animals and/or of increasing the disease resistance of animals and/or of increasing the immune response of animals and/or of establishing or maintaining a healthy gut microflora in animals and/or of reducing the pathogen shedding through the feces of animals, wherein the strains and/or preparations of the current invention or the compositions of the current invention, which comprise such strain(s), are administered to animals.

A further subject of the current invention is therefore also the use of strains and/or preparations and/or compositions of the current invention for enhancing the health of animals and/or for improving the general physical condition of animals and/or for improving the feed conversion rate of animals and/or for decreasing the mortality rate of animals and/or for increasing the survival rates of animals and/or for improving the weight gain of animals and/or for increasing the productivity of animals and/or for increasing the disease resistance of animals and/or for increasing the immune response of animals and/or for establishing or maintaining a healthy gut microflora in animals and/or for reducing the pathogen shedding through the feces of animals, wherein the strains and/or preparations of the current invention or the compositions of the current invention, which comprise such strain(s), are administered to animals.

A further subject of the current invention is therefore also the strains and preparations of the current invention as mentioned before and the compositions of the current invention, containing those strains, for enhancing the health of animals and/or for improving the general physical condition of animals and/or for improving the feed conversion rate of animals and/or for decreasing the mortality rate of animals and/or for increasing the survival rate of animals and/or for improving the weight gain of animals and/or for increasing the productivity of animals and/or for increasing the disease resistance of animals and/or for increasing the immune response of animals and/or for establishing or maintaining a healthy gut microflora in animals and/or for reducing the pathogen shedding through the feces of animals.

"Increasing the productivity of animals" refers, in particular, to any of the following: production of more or higher quality eggs, milk or meat or increased production of weaned offspring.

The methods and uses of the strains, preparations and compositions of the current invention can be therapeutic or non-therapeutic. In a particularly preferred embodiment of the current invention, the methods and uses are non-pharmaceutic, in particular, feeding applications.

Untreated manure of animals may have a detrimental environmental effect due to pathogenic bacteria and other ingredients, particularly with respect to the animals themselves and/or with respect to human beings coming in contact with the manure. This detrimental effect can be alleviated by either feeding the animals, or directly treating the manure or the bedding of the animals with the strains, compositions or preparations of the current invention. Therefore a further subject of the current invention is a method of controlling and/or avoiding detrimental environmental effects of manure or contaminated liquids, the method comprising the step of applying to manure, contaminated liquids, litter, a pit, or a manure pond at least one strain, one preparation and/or one composition according to the current invention. Preferably, the composition is applied in liquid form, for example by spraying, or as a powder, for example by strewing.

Detrimental bacteria may have a negative influence on the consistency of litter and in particular may effect a rather fluid or highly fluid litter, which might lead to foot pad lesions of poultry and which can be avoided by feeding the animals with the strains, compositions or preparations of the current invention. Therefore a further subject of the current invention is a method of controlling and/or improving the consistency of litter, in particular a method of ensuring a solid consistency of litter and/or a method of avoiding foot pad lesions, the method comprising the step of feeding animals, in particular poultry, at least one strain, one preparation and/or one composition according to the current invention.

The strains and preparations according to the invention can also be used for improving the quality of water. A further subject of the current invention is therefore also a method of controlling and/or improving the quality of water or aqueous solutions, in particular of drinking water and/or rearing water, comprising the step of applying to water or an aqueous solution at least one strain and/or at least one preparation and/or at least one composition of the current invention.

Further, the strains and preparations according to the invention can also be used for treating microbial diseases of plants. A further subject of the current invention is therefore also a method of treating and/or preventing microbial diseases of plants, in particular of cultivated plants, comprising the step of applying to the plants at least one strain and/or at least one preparation and/or at least one composition of the current invention. The application may be carried out in liquid form, such as by spraying, or in solid form, in particular as a powder.

By using the strains, preparations and compositions of the current invention preferably an improvement of at least one of the features mentioned above is realized, wherein realization of the feature preferably means an improvement of at least 1%, more preferably of at least 3 or at least 5%, in comparison to an adequate negative control. As a negative control, averages known in the animal husbandry field may be used, but preferably animals which are subjected to the same treatment as the animals tested are used, but without administration of the strains and/or preparations of the current invention.

In particular, the strains, preparations and compositions of the current invention may be administered or fed to an animal in an amount effective to inhibit and/or decrease the growth of pathogenic bacteria in the animal gut. Such pathogenic bacteria include *Clostridia, Listeria, Salmonella, Enterococci, Staphylococci, Aeromonas, Streptococci, Campylobacter, Escherichia coli*, and *Vibrio*. Relatedly, the methods of the present invention may be used to decrease the amount of pathogenic bacteria shed in animal feces. The methods of the present invention may also be used to maintain or increase the growth of beneficial bacteria, such as lactic acid bacteria, in the animal gut. By decreasing pathogenic bacteria and/or increasing or maintaining beneficial bacteria, the compositions of the present invention are able to maintain an overall healthy gut microflora.

Thus, a further subject of the current invention is a method of inhibiting and/or decreasing the growth of harmful or pathogenic bacteria and/or maintaining and/or increasing the growth of beneficial bacteria in an animal gut, wherein strains and/or preparations and/or compositions of the current invention are administered to animals and wherein the pathogenic bacteria are preferably selected from *Clostridia*, in particular *C. perfringens* and *C. difficile, Listeria*, in particular *L. monocytogenes, L. seeligeri* and *L. welshimeri, Salmonella*, in particular *S. enterica, S. gallinarum, S. pullorum, S. arizonae, S. typhimurium, S. enteritidis*, and *S. bongori, Enterococci*, in particular *E. faecalis, E. faecium* and *E. cecorum, Staphylococcus*, in particular *S. aureus, Aeromonas, Streptococci*, in particular *S. suis* and *S. gallinaceus, Campylobacter*, in particular *C. jejuni* and *C. coli, Escherichia coli*, and *Vibrio*, in particular *V. parahemolyticus* and *V. harveyi*, and the beneficial bacteria are preferably selected from lactic acid bacteria, in particular from *Lactobacilli*, and *Bifidobacteria*.

In a preferred embodiment of the invention, the amount of at least one pathogenic bacterium, in particular the amount of *C. perfringens*, is reduced by at least 0.5 log, and more preferably by at least 1 log, 2 log, or 3 log.

Thus, a further subject of the current invention are the strains, preparations and compositions of the current invention for inhibiting and/or decreasing the growth of pathogenic bacteria and/or for maintaining and/or increasing the growth of beneficial bacteria in an animal gut, wherein the pathogenic bacteria are preferably selected from *Clostridia*, in particular *C. perfringens* and *C. difficile, Listeria*, in particular *L. monocytogenes, L. seeligeri* and *L. welshimeri, Salmonella*, in particular *S. enterica, S. gallinarum, S. pullorum, S. arizonae, S. typhimurium, S. enteritidis*, and *S. bongori, Enterococci*, in particular *E. faecalis, E. faecium* and *E. cecorum, Staphylococcus*, in particular *S. aureus, Aeromonas, Streptococci*, in particular *S. suis* and *S. gallinaceus, Campylobacter*, in particular *C. jejuni* and *C. coli, Escherichia coli*, and *Vibrio*, in particular *V. parahemolyticus* and *V. harveyi*, and the beneficial bacteria are preferably selected from lactic acid bacteria, in particular from *Lactobacilli*, and *Bifidobacteria.*

The occurrence and/or increased growth of the pathogenic bacteria does or can lead to the outbreak of certain diseases. For example, the occurrence and/or increased growth of *Clostridium perfringens* can lead to the outbreak of gut diseases such as necrotic enteritis in poultry. The occurrence and/or increased growth of *Clostridium perfringens* can also lead to the outbreak of further diseases like bacterial enteritis, gangrenous dermatitis and colangiohepatitis. Even the mildest form of infection by *C. perfringens* can be accompanied by diarrhea, which results in wet litter that may lead to secondary diseases like foot pad dermatitis.

A further subject of the current invention is therefore a therapeutic composition comprising the strains and/or compositions of the current invention as mentioned before. A preferred subject in this context is therefore a therapeutic composition for treatment and/or prevention of necrotic enteritis, in particular sub-clinical necrotic enteritis, in animals, preferably poultry, comprising the strains and/or compositions of the current invention as mentioned before.

Another preferred subject in this context is a therapeutic composition for treatment and/or prevention of bacterial enteritis, gangrenous dermatitis, colangiohepatitis, clostridiosis, diarrhea and/or foot pad dermatitis, in animals, preferably poultry, comprising the strains and/or compositions of the current invention as mentioned before.

A further subject of the current invention is therefore also the treatment and/or prevention of a disease, in particular of a gut disease, preferably of necrotic enteritis, in particular of sub-clinical necrotic enteritis, in poultry, wherein a strain and/or composition and/or preparation of the current invention is administered to an animal in need thereof.

A further subject of the current invention is also the treatment and/or prevention of a disease, preferably a disease of poultry, selected from bacterial enteritis, gangrenous dermatitis, colangiohepatitis, clostridiosis, diarrhea and/or foot pad dermatitis, wherein a strain and/or composition and/or preparation of the current invention is administered to an animal in need thereof.

The strains and/or preparations and/or compositions of the current invention can be administered to animals in feed and/or drinking water over multiple days throughout the animal's life or during particular stages or portions of the animal's life. For example, the strains and/or compositions can be administered only in a starter diet or only in a finisher diet of farm animals.

A particular subject of the current invention is also a method of enhancing the health of human beings and/or of improving the general physical condition of human beings and/or of increasing the disease resistance of human beings and/or of increasing the immune response of human beings and/or of establishing or maintaining a healthy gut microflora in human beings, wherein the strains and/or preparations of the current invention or the compositions of the current invention are administered to human beings.

A further subject of the current invention is the use of strains and/or preparations and/or compositions of the current invention for enhancing the health of human beings and/or for improving the general physical condition of human beings and/or for increasing the disease resistance of human beings and/or for increasing the immune response of human beings and/or for establishing or maintaining a healthy gut microflora in human beings, wherein the strains and/or preparations of the current invention or the compositions of the current invention, which comprise such strain(s), are administered to human beings.

The compositions of the present invention, in particular the feed, food and pharmaceutical compositions as well as the drinking or rearing water, preferably comprise the strains of the current invention and are administered to animals at a rate of about $1\times10^3$ to about $2\times10^{12}$ CFU/g feed or ml water, in particular in a rate of about $1\times10^3$ or about $1\times10^4$ or about $1\times10^5$ or about $1\times10^6$ or about $1\times10^7$ or about $1\times10^8$ or about $1\times10^9$ or about $1\times10^{10}$ or about $1\times10^{11}$ or about $1\times10^{12}$ CFU/g feed or ml water, preferably in an amount of about $1\times10^4$ to about $1\times10^{10}$ CFU/g feed or ml water, and more preferably in an amount of $1\times10^4$ to $1\times10^7$ CFU/g feed or ml water.

Correspondingly, preferred amounts of the strains and/or preparations of the current invention in the feed, food and water compositions of the current invention range preferably from 0.1 wt.-% to 10 wt.-%, more preferably from 0.2 wt.-% to 5 wt.-%, in particular from 0.3 wt.-% to 3 wt.-%.

The methods of the present invention may be used for all kind of animals, in particular all kind of non-human and non-insect animals, more preferably all kind of vertebrates such as mammals, aquatic animals and birds.

Animals that may benefit from the current invention include but are not limited to farm animals, pets, exotic animals, zoo animals, aquatic animals, animals used for sports, recreation or work. Pets are preferably selected from dogs, cats, domestic birds and domestic exotic animals.

Aquatic animals are preferably selected from finfish and crustaceans which are preferably intended for human nutrition. These include, in particular, carp, tilapia, catfish, tuna, salmon, trout, barramundi, bream, perch, cod, shrimps, lobster, crabs, prawns and crayfish. Preferred types of salmon in this context are the Atlantic salmon, red salmon, masu salmon, king salmon, keta salmon, coho salmon, Danube salmon, Pacific salmon and pink salmon.

Further preferred aquatic animals are farming fish which are subsequently processed to give fish meal or fish oil. In this connection, the fish are preferably herring, pollack, menhaden, anchovies, capelin or cod.

In a further preferred embodiment, the animals are farm animals, which are raised for consumption or as food-producers, such as poultry, swine and ruminants.

The poultry may be selected from productive or domestic poultry, but also from fancy poultry or wild fowl.

Preferred productive poultry in this context are chickens, turkeys, ducks and geese. The productive livestock in this context is preferably poultry optimized for producing young stock or poultry optimized for bearing meat.

Preferred fancy poultry or wild fowl are peacocks, pheasants, partridges, chukkars, guinea fowl, quails, capercaillies, grouse, pigeons and swans, with quails being especially preferred.

Further preferred poultry are ratites, in particular ostriches and emus, as well as parrots.

Ruminants according to the current invention are preferably selected from cattle, goat and sheep. In one embodiment, the compositions of this invention may be fed to preruminants to enhance their health and, in particular, to decrease the incidence of diarrhea in these animals Preruminants are ruminants, including calves, ranging in age from birth to about twelve weeks.

The compositions of the current invention may comprise at least one carrier or typical feed ingredients or combinations thereof.

Suitable carriers are inert formulation ingredients added to improve recovery, efficacy, or physical properties and/or to aid in packaging and administration. Such carriers may be added individually or in combination. These carriers may be selected from anti-caking agents, anti-oxidation agents, bulking agents, and/or protectants. Examples of useful carriers include polysaccharides (in particular starches, maltodextrins, methylcelluloses, gums, chitosan and/or inulins), protein sources (in particular skim-milk powder and/or sweet-whey powder), peptides, sugars (in particular lactose, trehalose, sucrose and/or dextrose), lipids (in particular lecithin, vegetable oils and/or mineral oils), salts (in particular sodium chloride, sodium carbonate, calcium carbonate, chalk, limestone, magnesium carbonate, sodium phosphate, calcium phosphate, magnesium phosphate and/or sodium citrate), and silicates (in particular clays, in particular beolite clay, amorphous silica, fumed/precipitated silicas, zeolites, Fuller's earth, baylith, clintpolite, montmorillonite, diatomaceous earth, talc, bentonites, and/or silicate salts like aluminium, magnesium and/or calcium silicate). Suitable carriers for animal feed additives are set forth in the American Feed Control Officials, Inc.'s Official Publication, which publishes annually See, for example Official Publication of American Feed Control Officials, Sharon Krebs, editor, 2006 edition, ISBN 1-878341-18-9. The carriers can be added after concentrating the fermentation broth and/or during and/or after drying. Preferred carriers according to the invention are selected from calcium carbonate, diatomaceous earth and vegetable oil.

A preferred embodiment of the current invention are concentrate compositions, in particular feed additive compositions, i.e. compositions suitable for preparing a feed composition, which comprise at least one strain of the current invention and at least one carrier, wherein the at least one strain is preferably comprised in an amount of 0.1 to 10 wt.-%, more preferably in an amount of 0.2 to 5 wt.-%, in particular in an amount of 0.3 to 3 wt.-%, and most preferably in an amount of 0.4 to 2.2 wt.-%, and the at least one carrier is preferably comprised of an amount of at least 90 wt. %, preferably in an amount of 90 to 99.9 wt.-%, more preferably in an amount of 95 to 99.8 wt.-%, in particular in an amount of 97 to 99.7 wt.-%, and most preferably in an amount of 97.8 to 99.6 wt.-%, and wherein the carrier consists preferably substantially of limestone, in particular of limestone with smaller parts of diatomaceous earth and/or vegetable oil.

These preferred compositions of the current invention, which contain stabilized strains, can be used for the preparation of feed and pharmaceutical compositions as well as drinking and rearing water which preferably comprise the strains according to the invention in an amount as mentioned above. In a preferred embodiment, 200 to 1000 grams of such a concentrate composition, in particular 250, 500 or 1000 grams of such a concentrate composition, are used per ton of feed, drinking or rearing water to provide compositions which can be used for feeding animals. These concentrate compositions preferably comprise at least one strain of the current invention in an amount of $1\times10^9$ to $2\times10^{11}$ CFU, in particular $2\times10^9$ to 1×10" CFU, per g of the concentrate composition.

Starting from these concentrate compositions, feed and food compositions can be prepared by mixing the concentrate compositions with typical feed or food ingredients, respectively.

Typical animal feed ingredients which may be contained in the compositions according to the invention and/or used in the preparation of feed compositions starting from concentrate compositions according to the invention include one or more of the following: proteins, carbohydrates, fats, further probiotics, prebiotics, enzymes, vitamins, immune modulators, milk replacers, minerals, amino acids, coccidiostats, acid-based products and/or medicines, such as antibiotics.

Carbohydrates containing components which may be used according to the invention are for example forage, roughage, wheat meal, sunflower meal or soya meal, and mixtures thereof.

Protein-containing components which may be used according to the invention are for example soya protein, pea protein, wheat gluten or corn gluten, and mixtures thereof.

Fat-containing components which may be used according to the invention are in particular oils, of both animal and plant origin, like vegetable oils, for example soya bean oil, rapeseed oil, sunflower seed oil, flaxseed oil or palm oil, fish oil, and mixtures thereof.

Protein-containing components which additionally contain fats which may be used according to the invention are for example fish meal, krill meal, bivalve meal, squid meal or shrimp shells, as well as combinations thereof.

Further probiotics (DFM) which may be used according to the invention in combination with the strains and preparations of the invention are preferably bacteria selected from the species *Bacillus subtilis, Bacillus licheniformis, Bacillus lentus, Bacillus pumilus, Bacillus laterosporus, Bacillus coagulans, Bacillus alevi, Bacillus cereus, Bacillus badius, Bacillus thurigiensis, Enterococcus faecium*, and *Pediococcus acidilactici*. Preferred examples are *Bacillus licheniformis* DSM 32314 and derivatives thereof. *Bacillus licheniformis* DSM 32314 was deposited on May 12, 2016 under the terms of the Budapest Treaty on the International Recognition of the Deposit of Microorganisms for the Purpose of Patent Procedure. Deposit was made by Evonik Degussa GmbH at the international depositary Leibniz Institute DSMZ-German Collection of Microorganisms and Cell Culture, Inhoffenstr. 7 B, D-38124 Braunschweig GERMANY, which assigned it Accession Number DSM 32314.

Other preferred bacteria are *Bacillus subtilis* PB6 (as described in U.S. Pat. No. 7,247,299 and deposited as ATCC Accession No. PTA-6737), which is sold by Kemin under the trademark CLOSTAT®, *Bacillus subtilis* C-3102 (as described in U.S. Pat. No. 4,919,936 and deposited as FERM BP-1096 with the Fermentation Research Institute, Agency of Industrial Science and Technology, in Japan), sold by Calpis as CALSPORIN®, *Bacillus subtilis* DSM 17299, as sold by Chr. Hansen under the trademark GalliPro®, a mixture of *Bacillus subtilis* DSM 17299 and *Bacillus licheniformis* DSM 17236, as sold by Chr. Hansen under the trademark GalliProTect®, a mixture of *Bacillus licheniformis* and *Bacillus subtilis* spores sold by Chr. Hansen under the trademark BIOPLUS2B®, or *Bacillus coagulans* strains as described in U.S. Pat. No. 6,849,256. Other non-*Bacillus* probiotics, such as *Saccharomyces cerevisiae, Pichia pastoris, Aspergillus niger, Aspergillus oryzae*, or *Hansenula*, may also be used in compositions of the present invention. In particular in food compositions further probiotics which are known to be useful to the human health may be used such as lactic acid producing bacteria, in particular *lactobacilli*, or *Bifidobacteria*. If said further probiotics are not formulated as part of the compositions of the present invention, they may be administered together (either at the same time or at different times) with the compositions of the present invention.

Prebiotics which may be used according to the invention are preferably oligosaccharides, in particular selected from galactooligosaccharides, silayloligosaccharides, lactulose, lactosucrose, fructooligosaccharides, palatinose or isomaltose oligosaccharides, glycosyl sucrose, maltooligosaccharides, isomaltooligosaccharides, cyclodextrins, gentiooligosaccharides, soybean oligosaccharides, xylooligosaccharides, dextrans, pectins, polygalacturonan, rhamnogalacturonan, mannan, hemicellulose, arabinogalactan, arabinan, arabinoxylan, resistant starch, mehbiose, chitosan, agarose, inulin, tagatose, polydextrose, and alginate.

Enzymes which may be used in feed compositions according to the invention and which may aid in the digestion of feed, are preferably selected from phytases (EC 3.1.3.8 or 3.1.3.26), xylanases (EC 3.2.1.8), galactanases (EC 3.2.1.89), galactosidases, in particular alpha-galactosidases (EC 3.2.1.22), proteases (EC 3.4), phospholipases, in particular phospholipases A1 (EC 3.1.1.32), A2 (EC 3.1.1.4), C (EC 3.1.4.3), and D (EC 3.1.4.4), lysophospholipases (EC 3.1.1.5), amylases, in particular alpha-amylases (EC 3.2.1.1); lysozymes (EC 3.2.1.17), glucanases, in particular beta-glucanases (EC 3.2.1.4 or EC 3.2.1.6), glucoamylases, cellulases, pectinases, or any mixture thereof.

Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in e.g. WO 98/28408, WO 00/43503, and WO 03/066847.

Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont). Examples of commercially available proteases include Ronozyme® ProAct (DSM Nutritional Products).

Vitamins which may be used according to the invention are for example vitamin A, vitamin D3, vitamin E, vitamin K, e.g., vitamin K3, vitamin B12, biotin, choline, vitamin B1, vitamin B2, vitamin B6, niacin, folic acid and panthothenate, e.g., Ca-D-panthothenate, or combinations thereof.

Immune modulators which may be used are for example antibodies, cytokines, spray-dried plasma, interleukins, or interferons, or combinations thereof.

Minerals which may be used according to the invention are for example boron, cobalt, chloride, chromium, copper, fluoride, iodine, iron, manganese, molybdenum, selenium, zinc, calcium, magnesium, potassium, or sodium, or combinations thereof.

Amino acids which may be used according to the invention are for example lysine, alanine, threonine, methionine or tryptophan, or combinations thereof.

Thus, a further embodiment of the current invention is a method of preparing an animal feed composition comprising mixing at least one strain and/or at least one preparation and/or at least one concentrate composition of the current invention, in an amount effective to enhance animal health, with feed ingredients, such as proteins, lipids and/or carbohydrates, and optionally further beneficial substances, as mentioned above, to provide a feeding product. This method may comprise for example also a pelleting step.

Standard pelleting processes known to those of skill in the art may be used, including extrusion processing of dry or semi-moist feeds. Preferred pelleting temperatures are between about 65° C. and about 120° C.

The strains and compositions of the present invention can be obtained by culturing the strains of the current invention according to methods well known in the art, including by using the media and other methods as described for example in U.S. Pat. No. 6,060,051, EP0287699 or US2014/0010792. Conventional large-scale microbial culture processes include submerged fermentation, solid state fermentation, or liquid surface culture. Towards the end of fermentation, as nutrients are depleted, the cells of the strains begin the transition from growth phase to sporulation phase, such that the final product of fermentation is largely spores, metabolites and residual fermentation medium. Sporulation is part of the natural life cycle of these strains and is generally initiated by the cell in response to nutrient limitation. Fermentation is configured to obtain high levels of colony forming units of the *Bacillus subtilis* cells and to promote sporulation. The bacterial cells, spores and metabolites in culture media resulting from fermentation may be used directly or concentrated by conventional industrial methods, such as centrifugation, tangential-flow filtration, depth filtration, and evaporation. The concentrated fermentation broth may be washed, for example via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, as described above, may also be added post-drying.

Preparations of the strains of the current invention may be cell-free preparations or preparations containing cell debris or preparations containing a mixture of intact cells and cell debris. Cell-free preparations of the strains of the current invention can be obtained for example by centrifugation and/or filtration of fermentation broth. Depending on the technique used, these cell-free preparations may not be completely devoid of cells, but may still comprise a smaller amount of cells. As the cells secrete compounds like metabolites, enzymes and/or peptides into the surrounding medium, the supernatant of the cells comprises a mixture of such compounds, in particular metabolites, enyzmes and/or peptides, as secreted by the cells. Thus, in a preferred embodiment of the invention, the preparation of the strains is a supernatant of the fermentation broth.

Compositions comprising cell debris of the strains may be obtained by rupturing the cells applying techniques as known to those of skill in the art, for example by mechanical means or by applying high pressure. Depending on the degree of force applied, a composition comprising only ruptured cells or a composition comprising a mixture of cell debris and intact cells is obtained. Homogenization of the cells may be realized for example by utilizing a French cell press, sonicator, homogenizer, microfluidizer, ball mill, rod mill, pebble mill, bead mill, high pressure grinding roll, vertical shaft impactor, industrial blender, high shear mixer, paddle mixer, and/or polytron homogenizer. Suitable alternatives are enzymatic and/or chemical treatment of the cells.

Cell-free preparations of the current invention also comprise preparations which are obtained by first rupturing the cells by applying techniques as mentioned before and subsequently removing the cell debris and the remaining intact cells. Removing of the cell debris and remaining intact cells can be carried out in particular by centrifugation and/or filtration.

The preparations of the strains of the current invention may comprise as active compounds at least one metabolite, preferably a mixture of metabolites, as further described below, and/or at least one enzyme selected from proteases, in particular subtilisin, xylanases and/or cellulases, and/or at least one peptide, and/or combinations thereof.

A preparation containing an effective mixture of metabolites can be obtained for example according to the methods set forth in U.S. Pat. No. 6,060,051. In particular, the preparation can be obtained by precipitating the metabolites in the preparations mentioned using organic solvents like ethyl acetate and subsequently redissolving of the precipitated metabolites in an appropriate solvent. The metabolites may subsequently be purified by size exclusion filtration that groups metabolites into different fractions based on molecular weight cut-off.

The preparation containing an effective mixture of metabolites of the current invention preferably comprises at least five, more preferably at least 6, 7, 8, 9, 10 or 12, and most preferably all metabolites of the strains of the invention. The content of metabolites of the strain DSM 32315 is depicted in Table 5.1. The metabolites possess preferably a molecular weight of between 400 and 4000 Dalton, and more preferably of between 500 and 3500 Dalton.

Preferably an effective amount of the strains and/or preparations and/or compositions of the current invention is used in the embodiments of the current invention. The term "effective amount" refers to an amount which effects at least one beneficial effect to an animal and/or to the environment, in comparison to an animal or environment that has not been administered the strains and/or preparations and/or compositions of the current invention, but that has otherwise been treated the same.

In case of therapeutic applications, preferably a therapeutic amount of the strains and/or preparations and/or compositions of the current invention is used. The term "therapeutic amount" refers to an amount sufficient to ameliorate, reverse or prevent a disease state in an animal Optimal dosage levels for various animals can easily be determined by those skilled in the art, by evaluating, among other things, the composition's ability to (i) inhibit or reduce pathogenic bacteria in the gut at various doses, (ii) increase or maintain levels of beneficial bacteria and/or (iii) enhance animal health at various doses.

EXAMPLES

Example 1

Strain Characteristics Relevant to Survival in the Gastrointestinal Tract

*Bacillus subtilis* strains were screened from various environmental samples in order to obtain a superior strain as animal direct-fed microbial/probiotic. As the strain is intended to reach its full potential in the intestine of the target animal, the strain was pre-screened to withstand various environmental and gut related conditions. Strain spores were generated (Nicholson and Setlow 1990), washed and incubated at 80° C. for 20 minutes (pasteurization), then titrated in logarithmic/1 in 10 dilutions using veal infusion broth agar (VI, Difco™, no. 234420, Becton Dickinson GmbH, Heidelberg, Germany). The second highest dilution prior to no growth was stored at −80° C. and used as standardized starting point for all further assessments from spore state. To simulate gastric passage (Argenzio 2004a; Trampel and Duke 2004), survival of acid exposure was assessed based on Larsen et al. (2014). Growth of vegetative cells was furthermore assessed at low pH indicating growth under stomach/proventriculus and gizzard conditions, as well as in presence of up to 4 mM bile (B8631, CAS 8008-63-8, Sigma-Aldrich) at pH 7 in order to confirm strain growth at the proximal part of the small intestine right after clearance of the stomach or gizzard (Argenzio 2004b; Trampel and Duke 2004). Strain fitness in the anaerobe intestine (Argenzio 2004b; Trampel and Duke 2004) was assessed by inoculating standardized spore solutions under anaerobic conditions (AnaeroPak™, Thermo Fisher Scientific) in VI medium supplemented with 2.5 mM $KNO_3$ (Glaser et al. 1995). Furthermore the anaerobe proteolytic and cellulytic activity of strains was assessed on VI agar plates supplemented with 1% skim milk powder (70166, Sigma-Aldrich) or 0.1% water insoluble AZCL-HE cellulose (I-AZCEL, Megazyme International, Bray, Ireland). Osmotic stress, as also found in the gut (Argenzio 2004b; Trampel and Duke 2004), was assessed by determining growth on VI agar with addition of 5% NaCl (den Besten et al. 2009). Finally, spore heat stability was assessed to determine pelleting stability by exposing spores to 99° C. for 20 min (Palop et al. 1996) and subsequent inoculation on VI agar.

*Bacillus subtilis* strain DSM 32315 survived simulated gastric passage, growth of strain DSM 32315 was observed starting at pH 6. Strain DSM 32315 grew anaerobically and was able to degrade water-insoluble cellulose and protein under anaerobic conditions. Strain DSM 32315 was able to grow in presence of 2 and 4 mM bile, as well as in presence of 5% NaCl. Strain DSM 32315 reached an average spore count of $8.42\times10^8$ CFU/mL, and spores of strain DSM 32315 were viable after exposure to 99° C. for 20 min.

REFERENCES

Argenzio, R. A. (2004a). Secretion of the Stomach and Accessory Glands, p. 405-418. In: Reece, W. O. (ed.), Duke's Physiology of Domestic Animals; Twelfth Edition, Chapter 25; Cornell University Press, Ithaca, N.Y., USA.

Argenzio, R. A. (2004b). Digestive and Absorptive Functions of the Intestines, p. 419-437. In: Reece, W. O. (ed.), Duke's Physiology of Domestic Animals; Twelfth Edition, Chapter 26; Cornell University Press, Ithaca, N.Y., USA.

Dawson, R. M. C.; Elliot, D. C.; Elliot, W. H.; Jones, K. M. (1986). Data for Biochemical Research; 3rd edition, Oxford Science Publishing, United Kingdom.

Den Besten H M W, Mols M, Moezelaar R, Zwietering M H, Abee T. (2009). Phenotypic and transcriptomic analyses of mildly and severely salt-stressed *Bacillus cereus* ATCC 14579 cells. Appl Environ Microbiol. 75:4111-9.

Glaser, P., A. Danchin, F. Kunst, P. Zuber, and M. M. Nakano. (1995). Identification and isolation of a gene required for nitrate assimilation and anaerobic growth of *Bacillus subtilis*. J. Bacteriol. 177:1112-1115.

Nicholson W. L., Setlow P. Sporulation, germination and outgrowth. In: Harwood C R, Cutting S M, editors. Molecular biological methods for *Bacillus*. Chichester, England: John Wiley & Sons Ltd.; 1990. pp. 27-74.

Palop, A., Raso, J., Pagan, R., Condon, S. and Sala, F. J. (1996). Influence of pH on heat resistance of *Bacillus*

*licheniformis* in buffer and homogenized foods. International Journal of Food Microbiology 29, 1-10.

Trampel, D. W. and Duke, G. E. (2004). Avian Digestion, p. 488-500. In: Reece, W. O. (ed.), Duke's Physiology of Domestic Animals; Twelfth Edition, Chapter 29; Cornell University Press, Ithaca, N.Y., USA.

Example 2

Comparative Strain Performance Relative to State of the Art Direct-Fed Microbial (DFM)/Probiotic for Animal Nutrition—Quantitative Assessment of Bile Tolerance In order to assess the competitiveness of the *Bacillus subtilis* strain DSM 32315 selected from example 1, benchmarked analysis was performed using commercially available *Bacillus subtilis* strains DSM 17299 and DSM 5750. As both strains were identical as per every test performed, data in this and all following examples used strain DSM 17299 as reference. Readiness of strains to perform in the proximal small intestine in presence of bile at neutral pH right after gastric passage (Argenzio 2004b; Trampel and Duke 2004) was determined by strain growth in VIB media with addition 2 mM bile. Overnight culture with 50 uL candidate strain cell suspension and 10 mL VIB in 100 mL conical flask was incubated at 37° C. and 200 rpm, then approximately 50 uL of overnight culture was transferred to 100 well honeycomb plates (Oy Growth Curves Ab Ltd, former Thermo Labsy stems, Helsinky, Finland) with 1 mL VIB at pH 7 with 2 mM bile in order to obtain OD 0.2 per mL. Strain specific growth at 37° C. and 200 rpm was observed for 48 h with OD determined every 15 min using Bioscreeen C MBR with BioLink software package (Oy Growth Curves Ab Ltd). Averaged triplicate blank OD read of broth with bile only (blanks) were subtracted per culture at each time point before area under the curve (AUC) was calculated. Quantitative assessment for each strain was compared as area under the curve between 0-5 h (AUC5, in OD×time in h), area under the curve between 0-10 h (AUC10 in OD×time in h), and time until strains reached its maximum optical density (Tmax in h). Statistical analysis was performed using one-way ANOVA procedure of MiniTab® 16 Statistical Software (Minitab Inc., State College, Pa., USA). Results can be found in Table 2.1.

TABLE 2.1

Growth of *Bacillus subtilis* strain DSM 32315 and benchmark strain DSM 17299 in presence of 2 mM bile.

| Strain ID | AUC5 | AUC10 | Tmax |
|---|---|---|---|
| DSM 32315 | $0.884^{A}$ | $1.730^{A}$ | $17.5^{B}$ |
| DSM 17299 | $0.371^{B}$ | $1.381^{B}$ | $27.4^{A}$ |
| P-value | P < 0.001 | P = 0.001 | P < 0.001 |
| SEM | 0.013 | 0.020 | 0.2 |

AUC5, area under the curve between time point 0 and 5 h in optical density × h;
AUC10, area under the curve between time point 0 and 10 h in optical density × h;
Tmax, time in h until maximum optical density was reached;
SEM, pooled standard error of the mean;
$^{A, B}$ means that do not share a letter are significantly different.

In direct comparison, strain DSM 32315 reached its maximum OD in presence of 2 mM bile 10 h faster than the benchmark *Bacillus subtilis* strain DSM 17299. In addition, strain DSM 32315 grew 2.4 fold faster during the first 5 hours, and 1.3 fold faster during the first 10 h of the test, compared to growth of benchmark strain DSM 17299, respectively.

REFERENCES

Argenzio, R. A. (2004b). Digestive and Absorptive Functions of the Intestines, p. 419-437. In: Reece, W. O. (ed.), Duke's Physiology of Domestic Animals; Twelfth Edition, Chapter 26; Cornell University Press, Ithaca, N.Y., USA.

Trampel, D. W. and Duke, G. E. (2004). Avian Digestion, p. 488-500. In: Reece, W. O. (ed.), Duke's Physiology of Domestic Animals; Twelfth Edition, Chapter 29; Cornell University Press, Ithaca, N.Y., USA.

Example 3

Comparative Strain Performance Relative to State of the Art Direct-Fed Microbial (DFM)/Probiotic for Animal Nutrition—Growth in Presence of Short Chain Fatty Acids (SCFA)

Comparative growth of strains DSM 32142 and DSM 17299 was assessed in presence of short chain fatty acids as those are observed in the gut with increasing importance towards the large intestine (Argenzio 2004b; Trampel and Duke 2004). Tests were initiated using standardized spore solution as described in example 1 testing aerobe growth in VI medium at 37° C. and pH 6, read-out parameter was growth versus no growth. For this test, VI medium was adjusted to pH 6 using McIlvaine buffer (Palop et al. 1996) and subsequently supplemented with 0.05% acetic acid (HA, 537020, CAS 64-19-7, Sigma-Aldrich), 0.05% propionic acid (HP, P1386, CAS 79-09-4, Sigma-Aldrich) or 0.2% lactic acid (HL, W261106, CAS 50-21-5, Sigma-Aldrich). Results can be found in Table 3.1.

TABLE 3.1

Assessment of growth of *Bacillus subtilis* strains DSM 32315 and benchmark strain DSM 17299 in presence of short chain fatty acids at pH6.

| Strain ID | Acetic acid | Propionic acid | Lactic acid |
|---|---|---|---|
| DSM 32315 | Yes | Yes | Yes |
| DSM 17299 | No growth | No growth | No growth |

*Bacillus subtilis* strain DSM 32142 was able to grow at pH 6 in the presence of acetic, propionic and lactic acid, whereas strain DSM 17299 was unable to grow from spore stage under these conditions.

REFERENCES

Argenzio, R. A. (2004b). Digestive and Absorptive Functions of the Intestines, p. 419-437. In: Reece, W. O. (ed.), Duke's Physiology of Domestic Animals; Twelfth Edition, Chapter 26; Cornell University Press, Ithaca, N.Y., USA.

Palop, A., Raso, J., Pagan, R., Condon, S. and Sala, F. J. (1996). Influence of pH on heat resistance of *Bacillus licheniformis* in buffer and homogenized foods. International Journal of Food Microbiology 29, 1-10.

Trampel, D. W. and Duke, G. E. (2004). Avian Digestion, p. 488-500. In: Reece, W. O. (ed.), Duke's Physiology of Domestic Animals; Twelfth Edition, Chapter 29; Cornell University Press, Ithaca, N.Y., USA.

Example 4

Comparative Strain Performance Relative to State of the Art Direct-Fed Microbial (DFM)/Probiotic for Animal Nutrition—Quantitative Assessment of Enzymatic Activity Similar the to test conducted in Example 2, strains DSM 32315 and DSM 17299 were compared by evaluating respective carbohydrate degradation activity. Cellulase and Xylanase activity were determined as described in Larsen et al. (2014). Analysis was performed in three independent runs, then averaged as milliunits per microliter solution, statistical analysis was performed using one-way ANOVA procedure of MiniTab® 16 Statistical Software (Minitab Inc., State College, Pa., USA).

Results can be found in Table 4.1.

TABLE 4.1

Cellulase and xylanase activity of strains DSM 32315 and DSM 17299.

| Strain ID | Cellulase activity (mU/mL) | Xylanase activity (mU/mL) |
|---|---|---|
| DSM 32315 | 369.4 $^{A}$ | 33.5 $^{A}$ |
| DSM 17299 | 49.0 $^{B}$ | 16.0 $^{B}$ |
| P-value | P < 0.001 | P < 0.001 |
| SEM | 3.2 | 1.2 |

SEM, pooled standard error of the mean;
$^{A, B}$ means that do not share a letter are significantly different.

In direct comparison, strain DSM 32315 demonstrated a significant 7.5 fold increased cellulase and 2.1 fold increased xylanase activity comparing to benchmark strain DSM 17299.

REFERENCE

Larsen, N., Thorsen, L., Kpikpi, E. N., Stuer-Lauridsen, B., Cantor, M. D., Nielsen, B., Brockmann, E., Derkx, E. M. F. and Jespersen, L. (2014). Characterization of *Bacillus* spp. strains for use as probiotic additives in pig feed. Applied microbiology and biotechnology, 98(3), 1105-1118.

Example 5

Comparative Strain Performance Relative to State of the Art Direct-Fed Microbial (DFM)/Probiotic for Animal Nutrition—Expression of Metabolites and Pathogen Inhibition Similar to tests conducted in Example 2, strains DSM 32315 and benchmark strain DSM 17299 were compared by evaluating the respective number of metabolites expressed and pathogens inhibited in the respective media. For metabolite expression analysis, starter cultures were grown and tests performed as described in Scholz et al. (2011). From 10 mL Luria Bertami broth (LB, Thermo Fisher Scientific) culture grown for 24 h at 37° C. and 160 rpm in 100 mL flask, 100 uL were transferred to main culture. Main culture was grown either in 10 mL LB containing 0.2 mL/L KellyT trace metal solution (LBKelly, Scholz et al. 2011), or 10 mL Trypticase Soy Broth (Oxoid, Thermo Fisher Scientific) with 0.6% yeast extract (Y1625, CAS 8013-1-2, Sigma-Aldrich; resulting broth abbreviated TSBYE), both for 24 h at 37° C. at 160 rpm in 100 mL flasks. Of the main culture, 4 mL were combined with 2 mL n-Butanol in 15 mL test tube, vortexed for 3 min, then sonicated for 15 min. After centrifugation for 1 min at 5000 rpm, organic phase was transferred, vacuum dried and analyzed using High-performance liquid chromatography—electrospray ionization mass spectrometry (HPLC-ESI-MS; Chen et al. 2006). Every sample was measured in two different modes, negative and positive mode, and mass spectra were acquired. Resulting peaks as similarly reported in Teo and Tan (2005) were converted to molecular mass in Da. Results for comparison can be found in Table 5.1.

TABLE 5.1

Comparison of metabolites expressed by strains DSM 32315 and DSM 17299, respectively

| Molecular | Mass → | 504 Da | 529 Da | 571 Da | 967 Da | 994 Da | 1008 Da | 1022 Da | 1036 Da | 1050 Da | 1053 Da | 1463 Da | 1475 Da | 1477 Da | 1505 Da | 3398 Da | 3401 Da | 3419 Da |
|---|---|---|---|---|---|---|---|---|---|---|---|---|---|---|---|---|---|---|
| DSM | LBKelley | Yes | n/d | n/d | n/d | yes | yes | yes | yes | traces | n/d | Yes | Yes | Yes | Yes | n/d | yes | yes |
| 32142 | TSBYE | n/d | yes | yes | yes | n/d | yes | yes | yes | traces | n/d | n/d | n/d | n/d | n/d | n/d | n/d | n/d |
| | Combined | Yes | Yes | Yes | Yes | Yes | Yes | Yes | Yes | traces | | Yes | Yes | Yes | Yes | | Yes | Yes |
| DSM | LBKelley | n/d | n/d | n/d | n/d | n/d | traces | traces | traces | traces | n/d | n/d | n/d | n/d | n/d | yes | n/d | n/d |
| 17299 | TSBYE | n/d | n/d | n/d | yes | n/d | n/d | n/d | n/d | n/d | yes | n/d | n/d | n/d | n/d | n/d | n/d | n/d |
| | Combined | | | | yes | | traces | traces | traces | traces | yes | | | | | yes | | |

In addition, *Clostridium perfringens* inhibition via *Bacillus subtilis* bacteriocin production, as part of metabolites from table 5.1. but not closer investigated, was assessed using a well diffusion antagonism test (Parente et al. 1995). Four pathogenic *C. perfringens* candidates were tested: *C. perfringens* type strain ATCC 13124 from Teo and Tan (2005), as well as three pathogenic *C. perfringens* field isolates from poultry and swine, obtained from University of Leipzig, Faculty of Veterinary Medicine, Department of Bacteriology and Mycology, Prof. Dr. Christoph Baums, Potsdam, Germany. The *C. perfringens* type A-strains from Leipzig describe as follows: Strains 2300-1-17 and 2300-1-18 were isolated from a necrotic enteritis positive chicken digestive tract. Both strains produce α-toxin, strain 2300-1-17 also expressing NetB toxin (Sawa et al. 2013; Uzal et al. 2014) whereas strain 2300-1-18 tested positive for β2-toxin (Allaart et al. 2012). Strain 2300-1-19 was isolated from the digestive tract of a scouring piglet exhibiting symptoms of Clostridial type A enteritis (Songer and Uzal 2005). Growth conditions and media were described by Teo and Tan (2005). In brief, *Bacillus* strains were grown in 10 mL TSBYE and LBKelly starter culture for 24 h at 37° C. and 160 rpm in 100 mL flask in 5% $CO_2$ atmosphere, respectively. *Clostridium perfringens* starter cultures were cultivated anaerobically (AnaeroPak™, Thermo Fischer Scientific) in fluid thioglycolate broth (FTB, Becton Dickenson) for 24 h at 37° C. and 160 rpm in 100 mL flask, then spread with sterile cotton swab on agar plates (TSBYE with 1% agar, short TSAYE). Inoculated TSAYE plates were then incubated anaerobically overnight at 37° C. in order to obtain a lawn of *C. perfringens*. After overnight growth, three 9 mm diameter wells were cut into the agar with lawn: the 1$^{st}$ well was used as a non-inoculated control without culture; the 2nd well was inoculated with 100 uL not-*C. perfringens*-inhibiting *Bacillus* strain (*B. cereus* var. *toyoi*, NCIMB 40112); and the 3rd well was inoculated with 100 uL of *Bacillus subtilis* DSM 32315 or DSM 17299 starter culture. After 24 h incubation at 37° C., a zone of clearance in mm was determined measuring from the edge of the cut well to the border of the cleared lawn, each colony was measured twice (horizontally, vertically), then averaged. For each *Bacillus subtilis* antagonism test and media, analysis was performed in duplicate plate runs. Statistical analysis was performed using the one-way ANOVA procedure of MiniTab® 16 Statistical Software (Minitab Inc., State College, Pa., USA), results can be found in Table 5.2. for pathogen inhibition (strains grown in LBKelly), in Table 5.3 for pathogen inhibition (strains grown in TSBYE).

TABLE 5.2

Comparison of *Bacillus subtilis* DSM 32315 and DSM 17299 inhibitory capacity of pathogenic *C. perfringens* well diffusion antagonism assay (strains grown in TSBYE), values in mm clearance of pathogen.

| | Pathogenic *C. perfringens* | | | | |
|---|---|---|---|---|---|
| *B. subtilis* | Poultry Necrotic Enteritis strain 2300-1-17 | Poultry Necrotic Enteritis strain 2300-1-18 | Swine Clostridial Enteritis strain 2300-1-19 | Type strain ATCC 13124 | Average inhibition |
| DSM 32315 | 16.50 | 18.00 | 19.50 | 15.00 | 17.25 $^{A}$ |
| DSM 17299 | 2.00 | 0.00 | 6.00 | 2.00 | 2.50 $^{B}$ |
| P-value | | | | | <0.001 |
| SEM | | | | | 2.245 |

SEM, pooled standard error of the mean;
$^{A, B}$ means that do not share a letter are significantly different.

TABLE 5.3

Comparison of *Bacillus subtilis* DSM 32315 and DSM 17299 inhibitory capacity of pathogenic *C. perfringens* well diffusion antagonism assay (strains grown in TSBYE), values in mm clearance of pathogen.

| | Pathogenic *C. perfringens* → | | | | |
|---|---|---|---|---|---|
| *B. subtilis* ↓ | Poultry Necrotic Enteritis strain 2300-1-17 | Poultry Necrotic Enteritis strain 2300-1-18 | Swine Clostridial Enteritis strain 2300-1-19 | Type strain ATCC 13124 | Average inhibition |
| DSM 32315 | 8.00 | 13.00 | 7.00 | 2.50 | 7.63 $^{A}$ |
| DSM 17299 | 0.00 | 0.00 | 0.00 | 0.00 | 0.00 $^{B}$ |
| P-value | | | | | 0.01 |
| SEM | | | | | 3.05 |

SEM, pooled standard error of the mean;
$^{A, B}$ means that do not share a letter are significantly different.

REFERENCES

Allaart, J. G., de Bruijn, N. D., van Asten, A. J., Fabri, T. H., and Gröne, A. (2012). NetB-producing and beta2-producing *Clostridium perfringens* associated with subclinical necrotic enteritis in laying hens in the Netherlands. Avian Pathol., 41:541-546

Chen, X. H., Vater, J., Piel, J., Franke, P., Scholz, R., Schneider, K., Koumoutsi, A., Hitzeroth, G., Grammel, N., Strittmatter, A. W., Gottschalk, G, Süissmuth, R. and Borriss, R. (2006). Structural and functional characterization of three polyketide synthase gene clusters in *Bacillus amyloliquefaciens* FZB 42. Journal of bacteriology, 188 (11), 4024-4036.

Parente, E., Brienza, C., Moles, M., & Ricciardi, A. (1995). A comparison of methods for the measurement of bacteriocin activity. Journal of microbiological methods, 22(1), 95-108.

Sawa, G. S., Fernandes da Costa, S. P., Bokori-Brown, M., Naylor, C. E., Cole, A. R., Moss, D. S., Titball, R-W., and Basak, A. 2013. Molecular architecture and functional analysis of NetB, a pore-forming toxin from *Clostridium perfringens*. J Biol. Chem., 288: 3512-3522.

Scholz, R., Molohon, K. J., Nachtigall, J., Vater, J., Markley, A. L., Süssmuth, R. D., Mitchell, D. A. and Borriss, R. (2011) Plantazolicin, a novel microcin B17/streptolysin S-like natural product from *Bacillus amyloliquefaciens* FZB42. Journal of bacteriology, 193(1), 215-224.

Songer, J. G., and Uzal, F. A. (2005). *Clostridial enteric* infections in pigs. Journal of veterinary diagnostic investigation, 17(6), 528-536.

Teo, A. Y.-L. and Tan, H.-M. (2005). Inhibition of *Clostridium perfringens* by a novel strain of *Bacillus subtilis* from the gastrointestinal tracts of healthy chickens. Appl. Environm. Microbiol., 71:4185-90.

Uzal, F. A., Freedman, J C, Shrestha, A., Theoret, J. R., Garcia J., Awad, M. M., Adams, V., Moore, R. J., Rood, J. I., and McClane, B. A. (2014). Towards an understanding of the role of *Clostridium perfringens* toxins in human and animal disease. Future Microbiol., 9:361-377

Example 6

Comparison of Performance of Broilers Reared in India Fed a Novel *Bacillus subtilis*, a Competitor *Bacillus subtilis* Product or an Antibiotic Growth Promoter A broiler growth performance study was conducted, using as-hatched Vencobb 400 (Venkateshwara Hatcheries Pvt. Ltd, India) day old chicks in a floor pens with used litter. Four dietary treatments were randomly assigned, with twelve replicate pens per treatment containing 25 birds per pen. Birds were fed with one of the dietary treatments in three phases consisting of starter (1-14 days), grower (15-28 days) and finisher (29-42 days) phases. The basal diet was mainly based on corn-soybean meal (Table 6.1) containing 500 g/MT of dinotolmide to control coccidiosis. The basal diet also included 4% meat and bone meal (MBM), as additional challenge as MBM is a predisposing factor for development of necrotic enteritis caused by *Clostridium perfringens* in broiler chickens (M'Sadeqa et al. 2015). Four treatments were mainly based on corn-soybean meal (Table 6.1) and included; 1. Basal control (Control), 2. Control+50 g of Bacitracin Methylene Disalicyclate/MT of feed (BMD), 3. Control+a competitor product with *Bacillus subtilis* strain at 500 g/MT of feed with 1.6*$10^9$ cfu/g (DSM 17299), 4. Control+a *Bacillus subtilis* strain DSM 32315 at 250 g/MT containing 2.0*$10^9$ cfu/g (DSM 32315) Experimental treatments were fed ad libitum in mash form from 1-42 days of age Statistical analysis was performed using one-way ANOVA procedure and LSD post-test analysis with SAS vs9.4 (SAS Institute Inc., USA). The results of the treatments on body weight, feed conversion ratio and mortality are reported in Table 6.2.

TABLE 6.1

Ingredient and nutrient composition of basal diet.

| | Starter (1-14 d) | Grower (15-28 d) | Finisher (29-42 d) |
|---|---|---|---|
| Ingredients, % | | | |
| Corn | 53.98 | 62.27 | 64.54 |
| Soybean meal, 48% CP | 36.09 | 27.64 | 24.63 |
| Meat and bone meal | 4.00 | 4.00 | 4.00 |
| Soybean oil | 2.46 | 2.60 | 3.60 |
| Dicalcium phosphate 22 | 1.48 | 1.51 | 1.53 |
| Calcium carbonate | 0.39 | 0.45 | 0.16 |
| Premix (including vit-min mix) | 0.65 | 0.65 | 0.65 |
| Sodium chloride | 0.28 | 0.29 | 0.29 |
| Sodium bicarbonate | 0.10 | 0.10 | 0.10 |
| Choline chloride 50 | 0.10 | 0.10 | 0.10 |
| DL-Methionine | 0.29 | 0.23 | 0.22 |
| L-Lysine HCl | 0.12 | 0.13 | 0.14 |
| L-Threonine | 0.05 | 0.04 | 0.05 |
| Nutrient composition | | | |
| ME, kcal/kg | 2950 | 3050 | 3150 |
| CP, % | 23.50 | 20.08 | 18.83 |
| Ca | 1.00 | 1.00 | 1.00 |
| Available P | 0.45 | 0.45 | 0.45 |
| Lys | 1.36 | 1.14 | 1.06 |
| Met | 0.63 | 0.53 | 0.50 |
| M + C | 0.99 | 0.85 | 0.80 |
| Thr | 0.92 | 0.78 | 0.74 |
| Trp | 0.27 | 0.22 | 0.20 |
| Arg | 1.59 | 1.33 | 1.23 |
| Ile | 0.97 | 0.81 | 0.75 |
| Leu | 1.93 | 1.70 | 1.61 |
| Val | 1.08 | 0.92 | 0.86 |

TABLE 6.2

Animal performance between days 0 and 42, with and without diet supplementation with *B. subtilis* based feed additive or antibiotic growth promoter.

| | 1-21 d | | 1-42 d | |
|---|---|---|---|---|
| Treatment | BW, g | FCR, g/g | BW, g | FCR, g/g |
| 1. Control | 621.8 | 1.49 | 2278.2 | 1.76 |
| 2. BMD | 649.4 | 1.45 | 2321.4 | 1.74 |
| 3. DSM 17299 | 631.4 | 1.49 | 2281.8 | 1.76 |
| 4. DSM 32315 | 635.0 | 1.48 | 2309.2 | 1.73 |

TABLE 6.2-continued

Animal performance between days 0 and 42, with and without diet supplementation with *B. subtilis* based feed additive or antibiotic growth promoter.

| | 1-21 d | | 1-42 d | |
|---|---|---|---|---|
| Treatment | BW, g | FCR, g/g | BW, g | FCR, g/g |
| Difference | 13.2 | −0.01 | 31.0 | −0.03 |
| Relative % | 2.1% | −0.7% | 1.4% | −1.7% |

BW, average bird body weight in specified time period;
FCR, feed conversion ratio calculated as feed to gain in specified time period;
Control, no additives in basal diet;
BMD, treatment with addition of bacitracin methylene disalicylate to basal diet;
DSM 17299, treatment with addition of DSM 17299 to basal diet;
DSM 32315, treatment with addition of strain DSM 32315 to basal diet;
Difference, the numeric difference observed when DSM 32315 was compared to control;
Relative %, the difference between DSM 32315 and control as a percent change from control.

In the starter and grower period from 1-21 days DSM 32315 improved the FCR of broilers by 0.7% compared to the control. Body weight at 21 days was also improved by 2.1% when DSM 32315 was fed to broilers compared to the control. While these improvements were not to the extent of that observed when the very potent antibiotic growth promoter BMD was utilized, DSM 32315 did improve broiler performance in this period to a greater extent than DSM 17299.

Throughout the entire grow out period of broilers DSM 32315 was able to improve both body weight and feed conversion by 1.4% and −1.7% respectively. These improvements were again greater than those observed when the competitor product DSM 17299 was used. While day 42 body weight was still better in the antibiotic growth promoter group BMD, DSM 32315 treatment was able to reduce the FCR by an additional 0.01 (0.6%) compared to the BMD supplemented treatment group.

Overall, these results suggest that birds supplemented with DSM 32315 performed better than those fed a control or DSM 17299 and in at least some parameters was able to perform similarly to a highly effective antibiotic growth promoter.

REFERENCES

M'Sadeqa, S., Wua. S., Swicka, R. A. and M. Chocta (2015). Towards the control of necrotic enteritis in broiler chickens with in-feed antibiotics phasing-out worldwide. Animal Nutrition. 1:1-11.

Example 7

Comparison of Performance of Broilers Reared in Thailand Fed a Novel *Bacillus subtilis*, a Competitor *Bacillus subtilis* Product or an Antibiotic Growth Promoter A broiler growth performance study was conducted with male, Ross 308 (Aviagen Asia, Thailand) day old chicks placed in floor pens with used litter. There were four dietary treatments, 16 replicate pens per treatment and 12 birds per pen. Birds were fed with one of the dietary treatments in three phases consisting of starter (1-14 days), grower (15-28 days) and finisher (29-42 days) phases. The basal diet was mainly based on corn-soybean meal (Table 7.1) containing 60 g salinomycin/MT of feed to control coccidiosis. The basal diet also included 5% corn dried distiller's grains with solubles (DDGS), as the addition of DGGS, especially in starter diets, can reduce the rate of broiler growth (Lumpkins et al. 2004) and is a predisposing factor for development of necrotic enteritis caused by *Clostridium perfringens* in broiler chickens (Macklin et al. 2011). The four dietary treatments included; 1. Basal control (Control), 2. Control+20 g of Zinc Bacitracin /MT of feed (ZnB), 3. Control+a competitor product with *Bacillus subtilis* strain at 500 g/MT of feed with $1.6*10^9$ cfu/g (DSM 17299), 4. Control+a *Bacillus subtilis* strain DSM 32315 at 250 g/MT containing $20*10^9$ cfu/g (DSM 32315). The basal diet. Statistical analysis was performed using one-way ANOVA procedure and LSD post-test analysis with SAS vs9.4 (SAS Institute Inc., USA) Animal growth performance 0-42 days can be found in Table 7.2.

TABLE 7.1

Ingredient and nutrient composition of basal diet.

| | Starter (1-14 d) | Grower (15-28 d) | Finisher (29-42 d) |
|---|---|---|---|
| Ingredients, % | | | |
| Corn | 45.39 | 54.62 | 57.84 |
| Soybean meal, 44% CP | 40.00 | 30.82 | 27.00 |
| Corn DDGS | 5.00 | 5.00 | 5.00 |
| Soybean oil | 4.64 | 4.61 | 5.44 |
| Monocalcium phosphate | 1.59 | 1.61 | 1.63 |
| Calcium carbonate | 1.71 | 1.78 | 1.51 |
| Premix (including Vit-min mix) | 0.65 | 0.65 | 0.65 |
| Sodium chloride | 0.31 | 0.31 | 0.31 |
| Sodium bicarbonate | 0.10 | 0.10 | 0.10 |
| Choline chloride 50 | 0.10 | 0.10 | 0.10 |
| DL-Methionine | 0.28 | 0.22 | 0.21 |
| L-Lysine HCl | 0.14 | 0.15 | 0.17 |
| L-Threonine | 0.04 | 0.03 | 0.05 |
| Nutrient composition | | | |
| ME, kcal/kg | 2950 | 3050 | 3150 |
| CP, % | 23.01 | 19.63 | 18.22 |
| Ca | 1.00 | 1.00 | 0.90 |
| Available P | 0.45 | 0.45 | 0.45 |
| Lys | 1.35 | 1.12 | 1.04 |
| Met | 0.62 | 0.52 | 0.50 |
| M + C | 0.98 | 0.84 | 0.80 |
| Thr | 0.92 | 0.78 | 0.74 |
| Trp | 0.28 | 0.23 | 0.21 |
| Arg | 1.52 | 1.26 | 1.15 |
| Ile | 0.98 | 0.81 | 0.75 |
| Leu | 1.94 | 1.72 | 1.62 |
| Val | 1.08 | 0.92 | 0.85 |

TABLE 7.2

Animal performance between days 0 and 42, with and without diet supplementation with *B. subtilis* based feed additive or antibiotic growth promoter.

| | 1-42 d | | |
|---|---|---|---|
| Treatment | BW, g | FCR, g/g | Mortality % |
| 1. Control | 2845.0 | 1.83 | 4.17 |
| 2. ZnB | 2988.0 | 1.78 | 1.67 |
| 3. DSM 17299 | 2926.6 | 1.79 | 2.56 |
| 4. DSM 32315 | 3033.8 | 1.78 | 1.92 |

TABLE 7.2-continued

Animal performance between days 0 and 42, with and without diet supplementation with *B. subtilis* based feed additive or antibiotic growth promoter.

| | 1-42 d | | |
|---|---|---|---|
| Treatment | BW, g | FCR, g/g | Mortality % |
| Difference | 188.8 | −0.05 | −2.25 |
| Relative % | 6.9% | −2.7% | |

BW, average bird body weight in specified time period;
FCR, feed conversion ratio calculated as feed to gain in specified time period and adjusted for mortalities;
Control, no additives in basal diet;
ZnB, treatment with addition of zinc bacitracin;
DSM 17299, treatment with addition of DSM 17299 to basal diet;
DSM 32315, treatment with addition of strain DSM 32315 to basal diet;
Difference, the numeric difference observed when DSM 32315 was compared to control;
Relative %, the difference between DSM 32315 and control as a percent change from control.

During the entire grow-out period between 1 and 42 days, treatment with DSM 32315 was able to reduce the FCR by 2.7%. While this effect was also observed with the other treatment groups, BMD and DSM 17299, DSM 32315 treatment also resulted in the heaviest final body weight with a 6.9% increase from the control. Additionally, DSM 17299 was able to reduce the mortality of birds by 2.25% compared to untreated controls and by 0.64% compared to DSM 17299.

These results indicate that while all treatments were able to improve the feed conversion over the whole period, supplementation with DSM 32315 resulted in the heaviest final body weight of birds and a noticeable reduction in mortality.

REFERENCES

Lumpkins, B. S., Batal, A. B., & Dale, N. M. (2004). Evaluation of distillers dried grains with solubles as a feed ingredient for broilers. Poultry Science, 83(11), 1891-1896.

Macklin, K. S., Rose, L. N., and Dozier III, W. A. (2011). The effects of different levels of DDGS on necrotic enteritis development in broiler chickens. In Western Poultry Disease Conference, p. 123.

Example 8

Comparison of Performance of Broilers with and without Dietary Inclusion of a Novel *Bacillus subtilis* when Undergoing an Induced Necrotic Enteritis Challenge A necrotic enteritis challenge study was conducted, using male Ross 308 (Aviagen) day old chicks in floor pens. Three dietary treatments were randomly assigned, with eleven replicate pens per treatment containing 14 birds per pen. Birds were fed with one of the dietary treatments in three phases consisting of starter (1-11 days), grower (12-25 days) and finisher (26-35 days) phases. The basal diet was mainly based on corn-soybean meal (Table 8.1). The starter diet was prepared as 2 mm crumbled pellets and the grower and finisher diets as 4 mm pellets. The three treatments included; 1. Basal control (Control), 2. Positive Control+Narasin Coccidiostat (Monteban® G100, Elanco USA) 650 g/MT of feed (Narasin), 3. Control+a *Bacillus subtilis* strain DSM 32315 at 250 g/MT containing $20*10^9$ cfu/g (DSM 32315). Experimental treatments were fed ad libitum from 1-35 days of age.

Necrotic enteritis is a disease of chickens caused by a predisposing *Eimeria* infection with a synergistic *Clostridium perfringens* infection that usually occurs in 3-4 week old broilers (Timbermont et al. 2011). The Necrotic Enteritis challenge was induced in two parts; at 12 days of age each bird received an oral inoculation of 5000 *E. maxima oocytes* and at 16 days of age each bird received 300 µl of an overnight culture of a field strain of *Clostridium perfringens* that was originally isolated from ileal contents of broiler chicks suffering from necrotic enteritis. The results of the treatments on body weight, feed conversion ratio and mortality are reported in Table 8.2. The mortality is reported from day 11-35 to control for early bird losses due to chick quality that are not relevant to the disease challenge induced.

As footpad dermatitis has been connected to wet litter (Taira et al. 2014) and wet litter can be caused by gut health issues like necrotic enteritis (Timbermont et al. 2011), footpad lesion scores were also measured. The footpads were scored from sampled birds for pododermatitis (i.e., foodpad disease) using scale from 0 (representing no evidence of pododermatitis) to 4 (severe pododermatitis) based on the Welfare Quality 2009 (Rushen et al. 2011). The results of the treatments on footpad lesion scores is reported in Table 8.3. Specific bacterial groups (*Bacillus* spp. and *Clostridium perfringens*) were enumerated in ileal and caecal digesta samples from days 11, 18 and 35. Extracted DNA from the digesta samples was used in a quantitative PCR with primers specific to the species of interest. The results of the treatments on the molecular enumeration of bacterial groups (*Bacillus* spp. and *Clostridium perfringens*) at days 11, 18 and 35 is reported in Tables 8.4, 8.5 and 8.6 respectively.

TABLE 8.1

Ingredient and nutrient composition of basal diet.

| | Starter (1-11 d) | Grower (12-25 d) | Finisher (26-35 d) |
|---|---|---|---|
| Ingredients, % | | | |
| Corn | 52.15 | 57.12 | 61.93 |
| Soybean meal, 48% CP | 40.06 | 35.45 | 30.33 |
| Soybean oil | 3.28 | 3.68 | 4.12 |
| Monocalcium phosphate | 1.76 | 1.47 | 1.31 |
| Premix of trace elements and vitamins | 0.40 | 0.40 | 0.40 |
| Calcium carbonate | 1.40 | 1.18 | 1.11 |
| Sodium chloride | 0.37 | 0.37 | 0.37 |
| Choline chloride (60%) | 0.09 | 0.09 | 0.09 |
| DL-Methionine | 0.30 | 0.23 | 0.23 |
| L-Lysine HCl | 0.13 | 0.09 | 0.08 |
| L-Threonine | 0.04 | 0.03 | 0.02 |
| Nutrient composition | | | |
| ME, kcal/kg | 2950 | 3025 | 3100 |
| CP, % | 22.96 | 21.50 | 19.50 |
| Calcium | 1.00 | 0.85 | 0.78 |
| Available Phosphorous | 0.50 | 0.43 | 0.39 |
| Lysine | 1.35 | 1.19 | 1.10 |
| Methionine | 0.61 | 0.54 | 0.52 |
| Methionine + Cystine | 0.97 | 0.88 | 0.84 |
| Threonine | 0.92 | 0.82 | 0.76 |
| Tryptophan | 0.28 | 0.26 | 0.23 |
| Arginine | 1.55 | 1.45 | 1.29 |
| Isoleucine | 0.98 | 0.92 | 0.82 |
| Valine | 1.07 | 1.01 | 0.91 |

d, day;
CP, crude protein;
ME, metabolizable energy;
kcal, kilocalories;
kg, kilograms

TABLE 8.2

Animal performance between days 0 and 35, with and without diet supplementation with *B. subtilis* based feed additive or Narasin.

| | 1-35 days | | | |
|---|---|---|---|---|
| Treatment | BW, g | FCR, g/g | aFCR, g/g | Mortality, % |
| 1. Control | 2802.0 | 1.605 | 1.505 | 10.4 |
| 2. Narasin | 2778.4 | 1.431 | 1.425 | 1.3 |
| 3. DSM 32315 | 2845.5 | 1.493 | 1.456 | 3.9 |
| Difference | +43.5 | −0.112 | −0.049 | −6.5 |
| Relative % | +1.55 | +6.98 | +3.26 | |

BW, average bird body weight;
FCR, feed conversion ratio calculated as feed to gain in specified time period;
aFCR, feed conversion ratio calculated as feed to gain and adjusted for mortalities in specified time period;
Mortality, the mortality from day 11-35 as a percentage of the pen population;
Control, no additives in basal diet;
Narasin, treatment with addition of narasin coccidiostat to basal diet;
DSM 32315, treatment with addition of the novel *Bacillus subtilis* strain DSM 32315 to basal diet;
Difference, the numeric difference observed when DSM 32315 was compared to control;
Relative %, the difference between DSM 32315 and control as a percent change from control.

TABLE 8.3

Footpad lesion score, with and without diet supplementation with *B. subtilis* based feed additive or Narasin.

| Treatment | Footpad Lesion Score (0-4) |
|---|---|
| 1. Control | 2.29 |
| 2. Narasin | 0.41 |
| 3. DSM 32315 | 1.77 |
| Difference | −0.52 |
| Relative % | −22.7% |

Control, no additives in basal diet;
Narasin, treatment with addition of narasin coccidiostat to basal diet;
DSM 32315, treatment with addition of the novel *Bacillus subtilis* strain DSM 32315 to basal diet;
Difference, the numeric difference observed when DSM 32315 was compared to control;
Relative %, the difference between DSM 32315 and control as a percent change from control.

TABLE 8.4

Molecular enumeration of *Bacillus* species and *Clostridium perfringens* in the ileum and cecum of broilers, with and without diet supplementation with *B. subtilis* based feed additive or Narasin at 11 days of age.

| | Day 11 Ileum | | Day 11 Cecum | |
|---|---|---|---|---|
| Treatment | *C. perfringens* ($Log^{10}$ of gene copies/g) | *Bacillus* spp. ($Log^{10}$ of gene copies/g) | *C. perfringens* ($Log^{10}$ of gene copies/g) | *Bacillus* spp. ($Log^{10}$ of gene copies/g) |
| 1. Control | 4.51 | 4.75 | 6.39 | 4.10 |
| 2. Narasin | 4.18 | 5.68 | 6.38 | 5.24 |
| 3. DSM 32315 | 4.26 | 6.20 | 6.06 | 6.51 |
| Difference | −0.25 | +1.45 | −0.33 | +2.41 |

Control, no additives in basal diet;
Narasin, treatment with addition of narasin coccidiostat to basal diet;
DSM 32315, treatment with addition of the novel *Bacillus subtilis* strain DSM 32315 to basal diet;
Difference, the numeric difference observed when DSM 32315 was compared to control.

TABLE 8.5

Molecular enumeration of *Bacillus* species and *Clostridium perfringens* in the ileum and cecum of broilers, with and without diet supplementation with *B. subtilis* based feed additive or Narasin at 18 days of age.

| | Day 18 Ileum | | Day 18 Cecum | |
|---|---|---|---|---|
| Treatment | *C. perfringens* ($Log^{10}$ of gene copies/g) | *Bacillus* spp. ($Log^{10}$ of gene copies/g) | *C. perfringens* ($Log^{10}$ of gene copies/g) | *Bacillus* spp. ($Log^{10}$ of gene copies/g) |
| 1. Control | 6.27 | 4.71 | 6.17 | 4.58 |
| 2. Narasin | 4.60 | 4.94 | 4.87 | 4.54 |
| 3. DSM 32315 | 5.58 | 5.48 | 5.89 | 5.58 |
| Difference | −0.69 | +0.77 | −0.28 | +1.00 |

Control, no additives in basal diet;
Narasin, treatment with addition of narasin coccidiostat to basal diet;
DSM 32315, treatment with addition of the novel *Bacillus subtilis* strain DSM 32315 to basal diet;
Difference, the numeric difference observed when DSM 32315 was compared to control.

TABLE 8.6

Molecular enumeration of *Bacillus* species and *Clostridium perfringens* in the ileum and cecum of broilers, with and without diet supplementation with *B. subtilis* based feed additive or Narasin at 35 days of age.

| | Day 35 Ileum | | Day 35 Cecum | |
|---|---|---|---|---|
| Treatment | *C. perfringens* ($Log^{10}$ of gene copies/g) | *Bacillus* spp. ($Log^{10}$ of gene copies/g) | *C. perfringens* ($Log^{10}$ of gene copies/g) | *Bacillus* spp. ($Log^{10}$ of gene copies/g) |
| 1. Control | 5.36 | 4.77 | 6.64 | 5.06 |
| 2. Narasin | 4.03 | 4.84 | 4.81 | 5.23 |
| 3. DSM 32315 | 4.73 | 6.11 | 5.96 | 6.39 |
| Difference | −0.63 | +1.34 | −0.68 | +1.33 |

Control, no additives in basal diet;
Narasin, treatment with addition of narasin coccidiostat to basal diet;
DSM 32315, treatment with addition of the novel *Bacillus subtilis* strain DSM 32315 to basal diet;
Difference, the numeric difference observed when DSM 32315 was compared to control.

This study clearly provides evidence to support the beneficial effects of probiotic strain DSM 32315 on the performance of broilers facing a Necrotic Enteritis health challenge. The body weight of broilers fed DSM 32315 was increased, while the feed conversion ratio and mortality corrected feed conversion ratio was reduced compared to basal controls. These findings for the probiotic strain were similar to those of the positive control, Narasin, an anti-coccidiosial additive preventing the onset of Necrotic Enteritis in this model. Footpad lesions, associated with Necrotic Enteritis, were also reduced in broilers fed diets including strain DSM 32315 compared to basal diet control. This could be due to decreased moisture and pathogens in the litter, but this was not tested in this study.

At Day 11, 18 and 35 bacterial populations were enumerated in both the ileum and cecum of birds. In the treatment group fed diets containing the *Bacillus subtilis* strain DSM 32315, there were consistently more *Bacillus* enumerated at all time points and from both tissue sites. While some changes in *Bacillus* were observed in the Narasin treatment group compared to the control, these findings were very subtle and not consistent across all tissues and time points as was observed for the DSM 32315 treatment group.

When the causative agent of Necrotic Enteritis, *Clostridium perfringens*, was enumerated the DSM 32315 treatment group consistently showed a reduction in these pathogenic counts compared to the control group. This was similar to the positive control group, in which Narasin was added to the feed to prevent the onset of Necrotic Enteritis.

The data presented from this trial provide clear evidence as to the ability of DSM 32315 to inhibit the onset of Necrotic Enteritis and prevent subsequent losses due to loss of performance, mortality or footpad lesion condemnations at slaughter.

REFERENCES

Rushen J., A. Butterworth and J. C. Swanson (2011). Animal Behaviour and Well-Being Symposium: Farm animal welfare assurance: Science and application. *Journal of Animal Science* 89: 1219-1228

Taira K., T. Nagai, T. Obi and K. Takase (2014). Effect of Litter Moisture on the Development of Footpad Dermatitis in Broiler Chickens. J Vet Med Sci. 76(4): 583-586

Timbermont L., F. Haesebrouck, R. Ducatelle and F. Van Immerseel (2011). Necrotic enteritis in broilers: an updated review on the pathogenesis. Avian Pathol. 40(4): 341-347

Example 9

Assessment of Strain Tolerance to Feed Pellet Production and Feed Storage

To test the tolerance of *B. subtilis* DSM 32315 spores to the feed pelleting process, spores were added to a broiler grower diet (Table 9.1) that was then pelleted at 85° C. Prior to pelleting, ten replicate samples of the mixed feed were isolated for spore counts. Feed was then pelleted at 85° C. and additional five replicate samples were obtained. From the pre and post-pellet samples viable spores were cultured in dilution series, counted and calculated in feed concentrations. Results of the spore counts are presented in Table 9.2.

TABLE 9.1

Ingredients of the broiler diet used for pellet tolerance assessment.

| Ingredients | % Inclusion of Ingredients in Grower Diet |
|---|---|
| Wheat | 39.45 |
| Soybean meal, 48% CP | 26.97 |
| Corn | 25.00 |
| Soybean oil | 5.22 |
| Dicalcium phosphate 22 | 1.55 |
| Calcium carbonate | 0.79 |
| Sodium chloride | 0.28 |
| Sodium bicarbonate | 0.13 |
| BioLys ® | 0.24 |
| MetAMINO ® | 0.22 |
| ThreAMINO ® | 0.05 |
| Premix (vitamin + mineral) | 0.10 |

TABLE 9.2

Spore counts in feed pre- and post-pelleting.

| DSM 32315 Spore Count | Pre-Pelleted Feed | Post-Pelleted Feed |
|---|---|---|
| % Recovery of Spores | 100.0% | 79.9% |

% Recovery of Spores, calculated as the percentage of spores counted in relation to the spores counted pre-pelleting.

Spore counts post-pelleting remained within the 30% expected range from pre-pelleted feeds, signifying no significant loss of *B. subtilis* DSM 32315 spores during the pelleting process.

To test the stability of *B. subtilis* DSM 32315 spores in feed over time, spores were added to a broiler grower diet of the same formulation as previously described in Table 9.1. The feed was pelleted at 85° C. and three replicates of the diet were stored in a climate controlled chamber at 40° C. and 85% humidity. Spores were counted after pelleting (0 weeks in storage) as well as after 2, 4, 8 and 12 weeks of storage. Results of spore enumeration are presented in Table 9.3

TABLE 9.3

Recovery of DSM 32315 spores in pelleted feed after storage in climate chamber.

| | Storage Time | | | | |
|---|---|---|---|---|---|
| DSM 32315 Spore Count | 0 weeks | 2 weeks | 4 weeks | 8 weeks | 12 weeks |
| % Recovery of Spores | 100.0% | 84.1% | 97.7% | 86.4% | 82.6% |

% Recovery of Spores, calculated as the percentage of spores counted in relation to the spores counted at 0 weeks of storage directly after pelleting.

Spore counts in pelleted feed fluctuated over time, but remained within the expected 30% range of the spore counts obtained directly after pelleting. Therefore, it can be concluded that no significant loss of *B. subtilis* DSM 32315 spores was observed over 12 weeks of storage

Example 10

Well Diffusion Antagonism Tests with Respect to Different Pathogenic Strains A well diffusion antagonism test with 3 different pathogens, *Enterococcus cecorum* DSM 20683, *Streptococcus gallinaceus* DSM 15349 and *Streptococcus suis* ATCC 43765 was performed. *E. cecorum* is known to cause lameness, arthritis and osteomyelitis in broilers usually caused by an inflammation of a joint and/or bone tissue. Additional *E. cecorum* can cause an inflammation of the pericardium [Kense et al. 2011]. DSM 20683 was isolated from caecum of a chicken. *S. gallinaceus* can cause septicaemia in poultry. The gross lesions included splenomegaly, hepatomegaly, renomegaly and congestion. Multiple areas of necrosis and/or infarction in the liver and spleen associated with valvular endocarditis were also observed [Collins et al. 2002]. *S. suis* is an important pathogen in pigs and one of the most important causes of bacterial mortality in piglets after weaning causing septicemia, meningitis and many other infections [Goyette-Desjardins et al. 2014]. ATCC 43765 belongs to Serological group: R; serovar 2 and was isolated from pigs.

*Bacillus* strains were grown in 10 mL TSBYE (30 g/l TSB+6 g/l Yeast extract) or LB-Kelly (LB-Media supplemented with trace elements solution of DSMZ media 1032) for 16 h at 37° C. and 200 rpm in 100 mL shaking flask. The pathogenic strains were grown under suitable conditions as liquid culture to an optical density of 595 nm of at least 1, then 100 µl were spread with sterile spatula on the surface of agar plates. For *S. gallinaceus* BHI agar plates, for *E. cecorum* and *S. suis* TSBYE agar plates are used. Three 9 mm diameter wells were cut into the dried plates. 1$^{st}$ well was used as non-inoculated media control without culture, 2$^{nd}$ well was inoculated with 100 uL not-inhibiting *Bacillus* strain (*B. cereus* var. *toyoi*, NCIMB 40112), the 3$^{rd}$ well was inoculated with 100 uL of *Bacillus subtilis* DSM 32315 or DSM 17299 culture. After 24 h incubation under suitable conditions at 37° C., the zone of clearance in mm was determined measuring from the edge of the cut well to the border of the cleared lawn. Each colony was measured twice (horizontally, vertically), then averaged. The results can be found in table 10.1.

TABLE 10.1

Comparison of *Bacillus subtilis* DSM 32315 and DSM 17299 inhibitory capacity on pathogenic strains in well diffusion antagonism assays, values in mm clearance of pathogen.

| | Pathogen → | | |
|---|---|---|---|
| Probiotic ↓ | *E. cecorum* DSM 20683 | *S. gallinaceus* DSM 15349 | *S. suis* ATCC 43765 |
| DSM 32315 | 3.8 | 13.5 | 10.9 |
| DSM 17299 | 0.0 | 0.0 | 5.5 |

The data show that DSM 32315 is able to inhibit the growth of *E. cecorum*, *S. gallinaceus* and *S. suis* very effectively, in particular in comparison to DSM 17299.

REFERENCES

M J Kense, W J M Landman (2011). *Enterococcus cecorum* infections in broiler breeders and their offspring: molecular epidemiology. Avian Pathology Vol. 40, Iss. 6.

M D Collins, R A Hutson, E Falsen, E Ingana, M Bisgaard (2002). *Streptococcus gallinaceus* sp. nov., from chickens. International Journal of Systematic and Evolutionary Microbiology. 52: 1161-1164.

G Goyette-Desjardins, J-P Auger, J Xu, M Segura, M Gottschalk (2014). *Streptococcus suis*, an important pig pathogen and emerging zoonotic agent—an update on the worldwide distribution based on serotyping and sequence typing. Emerg Microbes Infect. 3(6):e45.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A feed or foodstuff comprising *Bacillus subtilis* strain DSM 32315, wherein said *Bacillus subtilis* strain inhibits the growth of *C. perfringens* bacteria and said feed or foodstuff inhibits the growth of *C. perfringens* in animals fed the feed or foodstuff;

a) wherein said *Bacillus subtilis* strain is able to grow in the presence of 2 mM bile; and b) wherein the feed or foodstuff further comprises at least one ingredient selected from the group consisting of: proteins, carbohydrates, fats, further probiotics, prebiotics, enzymes, vitamins, immune modulators, milk replacers, minerals, amino acids, coccidiostats, acid-based products, medicines, and combinations thereof.

2. The feed or foodstuff of claim 1, wherein the *Bacillus subtilis* strain comprises cellulase activity.

3. The feed or foodstuff of claim 1, wherein the *Bacillus subtilis* strain is present in the feed or foodstuff in an amount sufficient to reduce the growth of *C. perfringens* bacteria by at least 0.5 log in infected animals administered a diet of the feed or foodstuff on a daily basis and/or to reduce the mortality of infected animals by at least 2% compared to animals administered the same diet but where the feed of foodstuff does not comprise the *Bacillus subtilis* strain.

4. The feed or foodstuff of claim 1, wherein the *Bacillus subtilis* strain is present at $1\times10^3$ to $2\times10^{12}$ colony forming units (CFU) per gram of feed or foodstuff.

5. The feed or foodstuff of claim 1, wherein said *B. subtilis* DSM 32315 comprises one or more of the following:

a) a 16S rDNA sequence with the polynucleotide sequence of SEQ ID NO:1;

b) a yqfD sequence with the polynucleotide sequence of SEQ ID NO:2;

c) a gyrB sequence with the polynucleotide sequence of SEQ ID NO:3;

d) an rpoB sequence with the polynucleotide sequence of SEQ ID NO:4;

e) a groEL sequence with the polynucleotide sequence of SEQ ID NO:5.

6. The feed or foodstuff of claim 1, wherein said *Bacillus subtilis* strain is capable of degrading water-insoluble cellulose and protein under anaerobic conditions and/or has a cellulase activity of at least 200 mU/mL.

7. The feed or foodstuff of claim 1, wherein said *B. subtilis* strain exhibits a pathogen clearance of at least 10 mm in a well diffusion antagonism assay on LBKelly agar plates with respect to *C. perfringens* strain ATCC 13124.

8. The feed or foodstuff of claim 1, wherein said *B. subtilis* strain has xylanase activity and/or inhibits the growth of *Streptococcus suis* and *Streptococcus gallinaceus* bacteria and/or is able to grow in the presence of 0.05 wt.-% acetic acid, 0.05 wt.-% propionic acid and 0.2 wt.-% lactic acid.

9. The feed or foodstuff of claim 1, wherein the feed or foodstuff contains a cellulose comprising carbohydrate.

10. A composition comprising a mutant of *B. subtilis* DSM 32315 wherein said mutant:

a) comprises a DNA sequence identity of at least 99% to one or more of SEQ ID NO: 1-5;

b) inhibits the growth of *C. perfringens* bacteria;

c) is not found in nature;

d) is able to grow in the presence of 2 mM bile;

wherein the composition is a feed or foodstuff and further comprises at least one further feed or food ingredient selected from the group consisting of: proteins, carbohydrates, fats, further probiotics, prebiotics, enzymes, vitamins, immune modulators, milk replacers, minerals, amino acids, coccidiostats, acid-based products, medicines, and combinations thereof.

11. The composition of claim 10, wherein said mutant of *B. subtilis* DSM 32315 is a genetically engineered bacteria or said mutant has a mutation resulting from growing bacteria in the presence of a mutagen.

12. The composition of claim 10, wherein said mutant of *B. subtilis* DSM 32315 exhibits a pathogen clearance of at least 10 mm in a well diffusion antagonism assay on LBKelly agar plates with respect to *C. perfringens* strain ATCC 13124 and/or comprises a cellulase activity of at least 200 mU/mL, and/or a xylanase activity of at least 15 mU/mL and/or inhibits the growth of *S. suis* and *S. gallinaceus* bacteria.

13. The composition of claim 10, wherein said mutant of *B. subtilis* DSM 32315 comprises one or more of the following:

a) a 16S rDNA sequence with a sequence at least 99% identical to the polynucleotide sequence of SEQ ID NO:1;

b) a yqfD sequence with a sequence at least 99% identical to the polynucleotide sequence of SEQ ID NO:2;

c) a gyrB sequence with a sequence at least 99% identical to the polynucleotide sequence of SEQ ID NO:3;

d) an rpoB sequence at least 99% identical to the polynucleotide sequence of SEQ ID NO:4;

e) a groEL sequence at least 99% identical to the polynucleotide sequence of SEQ ID NO:5.

14. The composition of claim 13, wherein said mutant of DSM 32315 comprises cellulase activity and also comprises all of the sequences of paragraphs a)-e).

15. The composition of claim 10, wherein said mutant of *B. subtilis* DSM 32315 comprises xylanase activity and/or inhibits the growth of *Streptococcus suis* and *Streptococcus gallinaceus* bacteria and/or is able to grow in the presence of 0.05 wt.-% acetic acid, 0.05 wt.-% propionic acid and 0.2 wt.-% lactic acid.

16. A composition comprising a fermentation broth of either:

a) *B. subtilis* DSM 32315; or b) a mutant of *B. subtilis* DSM 32315, wherein the said mutant:

i) comprises a DNA sequence identity of at least 99% to one or more of SEQ ID NO: 1-5;

ii) inhibits the growth of *C. perfringens* bacteria;

iii) is not found in nature;

iv) is able to grow in the presence of 2 mM bile;

wherein the fermentation broth inhibits the growth of *C. perfringens, Salmonella gallinaceus*, and *Streptococcus suis* bacteria and is optionally concentrated and/or dried.

17. The composition of claim 16, wherein said composition is a feed or foodstuff and said feed or foodstuff:

a) inhibits the growth of *C. perfringens* in animals fed the feed or foodstuff;

b) comprises at least one ingredient selected from the group consisting of: proteins, carbohydrates, fats, further probiotics, prebiotics, enzymes, vitamins, immune modulators, milk replacers, minerals, amino acids, coccidiostats, acid-based products, medicines, and combinations thereof.

18. The composition of claim 16, wherein the composition has cellulase activity and xylanase activity.

19. The composition of claim 18, wherein the composition contains a cellulose containing carbohydrate.

20. The composition of claim 16, wherein the fermentation broth is concentrated and/or dried.

21. The composition of claim 16, wherein the fermentation broth is a cell-free composition.

* * * * *